United States Patent
Kochem et al.

(10) Patent No.: US 11,298,182 B2
(45) Date of Patent: *Apr. 12, 2022

(54) FUNDUS BUMPER MECHANICAL REFERENCE FOR EASIER MECHANISM DEPLOYMENT

(71) Applicant: Hologic, Inc., Marlborough, MA (US)

(72) Inventors: Thomas C. Kochem, Watertown, MA (US); Daniel A. Beaudet, Lexington, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/840,316

(22) Filed: Apr. 3, 2020

(65) Prior Publication Data

US 2020/0229865 A1    Jul. 23, 2020

Related U.S. Application Data

(63) Continuation of application No. 15/065,254, filed on Mar. 9, 2016, now Pat. No. 10,624,694, which is a
(Continued)

(51) Int. Cl.
*A61B 18/14* (2006.01)
*A61F 6/18* (2006.01)
(Continued)

(52) U.S. Cl.
CPC ...... *A61B 18/1485* (2013.01); *A61B 17/0218* (2013.01); *A61B 17/42* (2013.01);
(Continued)

(58) Field of Classification Search
CPC ........... A61B 18/1485; A61B 17/0218; A61B 17/42; A61B 2018/00577;
(Continued)

(56) References Cited

U.S. PATENT DOCUMENTS 2,190,383 A   2/1940  Newman
4,489,732 A  12/1984  Hasson
(Continued)

FOREIGN PATENT DOCUMENTS

AU   2005319523 A1  6/2006
CA      2591535 A1  6/2006
(Continued)

OTHER PUBLICATIONS

Shepherd et al. 10.1073/pnas-1116564108_SI(2)—Supporting Information—pp. 1-7; Mar. 8, 2013.
(Continued)

*Primary Examiner* — Camtu T Nguyen
(74) *Attorney, Agent, or Firm* — Vista IP Law Group, LLP

(57) ABSTRACT

Intrauterine devices and methods for facilitating deployment thereof using a bumper are disclosed. In one embodiment, an intrauterine device comprises a structure including a first central support member and a deployment mechanism coupled to the first central support member. The intrauterine device further comprises a bumper positioned at a distal end of a second central support member and at a more distal position relative to a distal end of the structure so as to prevent the distal end of the structure from contacting the fundus of the uterus of a patient during deployment of the deployment mechanism. In another embodiment, the intrauterine device comprises a bumper coupled to the deployment mechanism and configured to move from a more distal to a more proximal position relative to a distal end of the structure.

14 Claims, 20 Drawing Sheets

Related U.S. Application Data continuation of application No. 13/758,188, filed on Feb. 4, 2013, now Pat. No. 9,333,111.

(51) Int. Cl.
  *A61B 17/02* (2006.01)
  *A61B 17/42* (2006.01)
  *A61B 18/00* (2006.01)
  *A61B 90/00* (2016.01)

(52) U.S. Cl.
  CPC .......... *A61B 17/4241* (2013.01); *A61F 6/18* (2013.01); *A61B 2017/4216* (2013.01); *A61B 2018/00065* (2013.01); *A61B 2018/00071* (2013.01); *A61B 2018/00214* (2013.01); *A61B 2018/00559* (2013.01); *A61B 2018/00577* (2013.01); *A61B 2018/1465* (2013.01); *A61B 2090/065* (2016.02); *A61B 2090/08021* (2016.02)

(58) Field of Classification Search
  CPC .......... A61B 2018/00505; A61B 2018/00559; A61F 6/18
  See application file for complete search history.

(56) References Cited

U.S. PATENT DOCUMENTS

| | | |
|---|---|---|
| 4,946,440 A | 8/1990 | Hall |
| 5,002,558 A | 3/1991 | Klein et al. |
| 5,188,596 A | 2/1993 | Condon et al. |
| 5,217,466 A | 6/1993 | Hasson |
| 5,235,966 A | 8/1993 | Jamner |
| 5,314,443 A | 5/1994 | Rudnick |
| 5,358,496 A | 10/1994 | Ortiz et al. |
| 5,501,681 A | 3/1996 | Neuwirth et al. |
| 5,505,730 A | 4/1996 | Edawards |
| 5,542,928 A | 8/1996 | Evans et al. |
| 5,558,672 A * | 9/1996 | Edwards .............. A61N 1/06 606/41 |
| 5,702,438 A | 12/1997 | Avitall |
| 5,769,880 A | 6/1998 | Truckai et al. |
| 5,776,129 A | 7/1998 | Mersch |
| 5,830,179 A | 11/1998 | Mikus et al. |
| 5,836,947 A | 11/1998 | Fleischman |
| 5,882,290 A | 3/1999 | Kume |
| 5,891,094 A | 4/1999 | Masterson et al. |
| 5,913,856 A | 6/1999 | Chia et al. |
| 5,935,098 A | 8/1999 | Blaisdell et al. |
| 6,096,047 A | 8/2000 | Smit |
| 6,159,207 A | 12/2000 | Yoon |
| 6,261,219 B1 | 7/2001 | Meloul et al. |
| 6,283,988 B1 | 9/2001 | Laufer et al. |
| 6,450,977 B1 | 9/2002 | Baxter-Jones |
| 6,450,983 B1 | 9/2002 | Rambo |
| 6,468,292 B1 | 10/2002 | Mollenauer et al. |
| 6,540,655 B1 | 4/2003 | Chin et al. |
| 6,547,784 B1 | 4/2003 | Thompson et al. |
| 6,607,477 B1 | 8/2003 | Longton et al. |
| 6,607,545 B2 | 8/2003 | Kammerer et al. |
| 6,635,054 B2 | 10/2003 | Fjield et al. |
| 6,663,626 B2 | 12/2003 | Truckai et al. |
| 6,706,026 B1 | 3/2004 | Goldstein et al. |
| 6,796,976 B1 | 9/2004 | Chin et al. |
| 6,813,520 B2 | 11/2004 | Truckai et al. |
| 6,840,937 B2 | 1/2005 | Van Wyk |
| 6,929,642 B2 | 8/2005 | Xiao et al. |
| 6,942,648 B2 | 9/2005 | Schaible et al. |
| 6,960,203 B2 | 11/2005 | Xiao et al. |
| 7,101,367 B2 | 9/2006 | Xiao et al. |
| 7,105,007 B2 | 9/2006 | Hibler |
| 7,381,208 B2 | 6/2008 | van der Walt et al. |
| 7,500,973 B2 | 3/2009 | Vancelette et al. |
| 7,512,445 B2 | 3/2009 | Truckai et al. |
| 7,625,368 B2 | 12/2009 | Schechter et al. |
| 7,674,259 B2 | 3/2010 | Shadduck |
| 7,963,962 B2 | 6/2011 | Thompson et al. |
| 8,007,449 B2 | 8/2011 | Kotmel et al. |
| 8,025,656 B2 | 9/2011 | Gruber et al. |
| 8,298,213 B2 | 10/2012 | Singh |
| 8,348,864 B2 | 1/2013 | Kotmel et al. |
| 8,372,068 B2 | 2/2013 | Truckai |
| 8,597,289 B2 | 12/2013 | Layton, Jr. et al. |
| 2002/0058951 A1 | 5/2002 | Fiedler |
| 2002/0068934 A1 | 6/2002 | Edwards et al. |
| 2002/0082667 A1 | 6/2002 | Shadduck |
| 2002/0177846 A1 | 11/2002 | Muller et al. |
| 2002/0183730 A1 | 12/2002 | Reu et al. |
| 2003/0032953 A1 | 2/2003 | VanDusseldorp |
| 2004/0002698 A1 | 1/2004 | Xiao et al. |
| 2004/0098013 A1 | 5/2004 | Ciaglia et al. |
| 2004/0122463 A1 | 6/2004 | Hibler |
| 2005/0061329 A1 | 3/2005 | Tran et al. |
| 2005/0085827 A1 | 4/2005 | G. et al. |
| 2005/0085880 A1 | 4/2005 | Truckai et al. |
| 2005/0159644 A1 | 7/2005 | Takano |
| 2005/0209627 A1 | 9/2005 | Kick et al. |
| 2005/0234543 A1 | 10/2005 | Glaser et al. |
| 2005/0240211 A1 | 10/2005 | Sporri |
| 2005/0283178 A1 | 12/2005 | Flagle et al. |
| 2006/0004398 A1 | 1/2006 | Binder et al. |
| 2006/0047269 A1 | 3/2006 | Reever et al. |
| 2006/0135887 A1 | 6/2006 | Sampson et al. |
| 2006/0200185 A1 | 9/2006 | Marchek et al. |
| 2006/0212062 A1 | 9/2006 | Farascioni |
| 2006/0271034 A1 | 11/2006 | Swanson |
| 2007/0005089 A1 | 1/2007 | Smith et al. |
| 2007/0032814 A1 | 2/2007 | Hibler |
| 2007/0066990 A1 | 3/2007 | Marsella et al. |
| 2007/0083194 A1 * | 4/2007 | Kunis .............. A61B 18/1815 606/41 |
| 2007/0142752 A1 | 6/2007 | Kotmel et al. |
| 2008/0039864 A1 | 2/2008 | Feuer et al. |
| 2008/0039865 A1 | 2/2008 | Shaher et al. |
| 2008/0109010 A1 | 5/2008 | Feuer et al. |
| 2008/0135053 A1 | 6/2008 | Gruber et al. |
| 2008/0208189 A1 | 8/2008 | Van Wyk et al. |
| 2008/0245374 A1 | 10/2008 | Agnew |
| 2008/0249534 A1 | 10/2008 | Gruber et al. |
| 2008/0259730 A1 | 10/2008 | Di Federico |
| 2008/0312644 A1 | 12/2008 | Fourkas et al. |
| 2009/0054868 A1 | 2/2009 | Sharkey et al. |
| 2009/0054870 A1 | 2/2009 | Sharkey et al. |
| 2009/0125010 A1 | 5/2009 | Sharkey et al. |
| 2009/0137970 A1 | 5/2009 | George et al. |
| 2009/0149846 A1 | 6/2009 | Hoey et al. |
| 2009/0270989 A1 | 10/2009 | Conner et al. |
| 2009/0292307 A1 | 11/2009 | Razack |
| 2010/0004651 A1 | 1/2010 | Biyani |
| 2010/0094074 A1 | 4/2010 | Mark et al. |
| 2010/0094075 A1 | 4/2010 | Mark |
| 2010/0100091 A1 | 4/2010 | Truckai |
| 2010/0114089 A1 | 5/2010 | Truckai et al. |
| 2010/0114147 A1 | 5/2010 | Biyani |
| 2010/0228239 A1 | 9/2010 | Freed |
| 2010/0256623 A1 | 10/2010 | Nicolas et al. |
| 2010/0268244 A1 | 10/2010 | Hansen et al. |
| 2010/0274260 A1 | 10/2010 | D'Arpiany et al. |
| 2011/0160715 A1 | 6/2011 | Ostrovsky et al. |
| 2011/0190783 A1 | 8/2011 | Calderon |
| 2011/0208178 A1 | 8/2011 | Truckai |
| 2011/0213231 A1 | 9/2011 | Hall et al. |
| 2012/0065632 A1 | 3/2012 | Shadduck |
| 2012/0101332 A1 | 4/2012 | Truckai et al. |
| 2012/0209281 A1 | 8/2012 | Truckai |
| 2012/0224558 A1 | 9/2012 | Truckai |
| 2013/0206147 A1 | 8/2013 | Skalyni |
| 2013/0269705 A1 | 10/2013 | Kochem et al. |
| 2014/0200591 A1 | 7/2014 | Sullivan et al. |
| 2014/0276234 A1 | 9/2014 | Hines et al. |
| 2014/0276726 A1 | 9/2014 | Model |

(56) References Cited

U.S. PATENT DOCUMENTS

FOREIGN PATENT DOCUMENTS

| EP | 1827231 A1 | 9/2007 |
|---|---|---|
| WO | 2006/068807 A1 | 6/2006 |
| WO | 2010053700 A1 | 5/2010 |
| WO | 2011084616 A2 | 7/2011 |

OTHER PUBLICATIONS

The HTA ProCerva Procedure Sheath Seal mechanism Demonstration, Boston Scientific. Date unknown. 1 page.
International Search Report issued in corresponding International Application No. PCT/US2014/014544, dated Jun. 10, 2014, 3 pages.
International Search Report issued in corresponding International Application No. PCT/US2013/606113 dated Dec. 12, 2013.
International Search Report issued in corresponding International Application No. PCT/US2014/014895, dated Mar. 27, 2014.
Gilbert Surgical Instruments, "Sounds", various products, <http://www.gilbertsurgical.com/html/fm/sounds.html>, 2000, 1 page.
Life Care Supplies, "OB/GYM Instruments—Sklar Surgical Instruments—Uterine Sounds", various products, <http://lcsupplies.com/products/obgyn.sound.htm>, undated—downloaded on Mar. 31, 2005, 1 page.
Notification of Transmittal of the International Search Report and Written Opinion of the International Searching Authority, or the Declaration of International Application No. PCT/US13/60613, dated Sep. 16, 2013, 19 pages.
Ole Daniel Emerson—Who Named It?, a description of Simpson's Uterine Sound (Sir James Young Simpson), <http://www.whonamedit.com/synd.cfm/2993.html>, 1994 -2001, 1 page.
Pelican Healthcare Ltd., "Pelican Disposable Sound—Tecnical Data Sheet", <http://www.pelicanhealthcare.co.uk/pdfs/sound.pdf>, undated, accessed on Mar. 31, 2005, 1 page.
Pelican Healthcare Ltd., "Pelican Disposable Uterine Sound—Sterile", Product Description, <http://www.pelicanhealthcare.co.uk/sound.htm>, undated, accessed on Mar. 31, 2005, 1 page.
Track of Surgical, "Assorted Uterine Sounds", various products, <http://www.track.com.pk/assorted2.htm>, undated—last printed Mar. 31, 2005, 2 pages.
Westons Internet Sales, "Uterine Sound", various products, <http://www.westons.com/acatalog/Online_Catalogue_Uterine_sound_326.html>, last modified Feb. 23, 2005, 2 pages.

\* cited by examiner

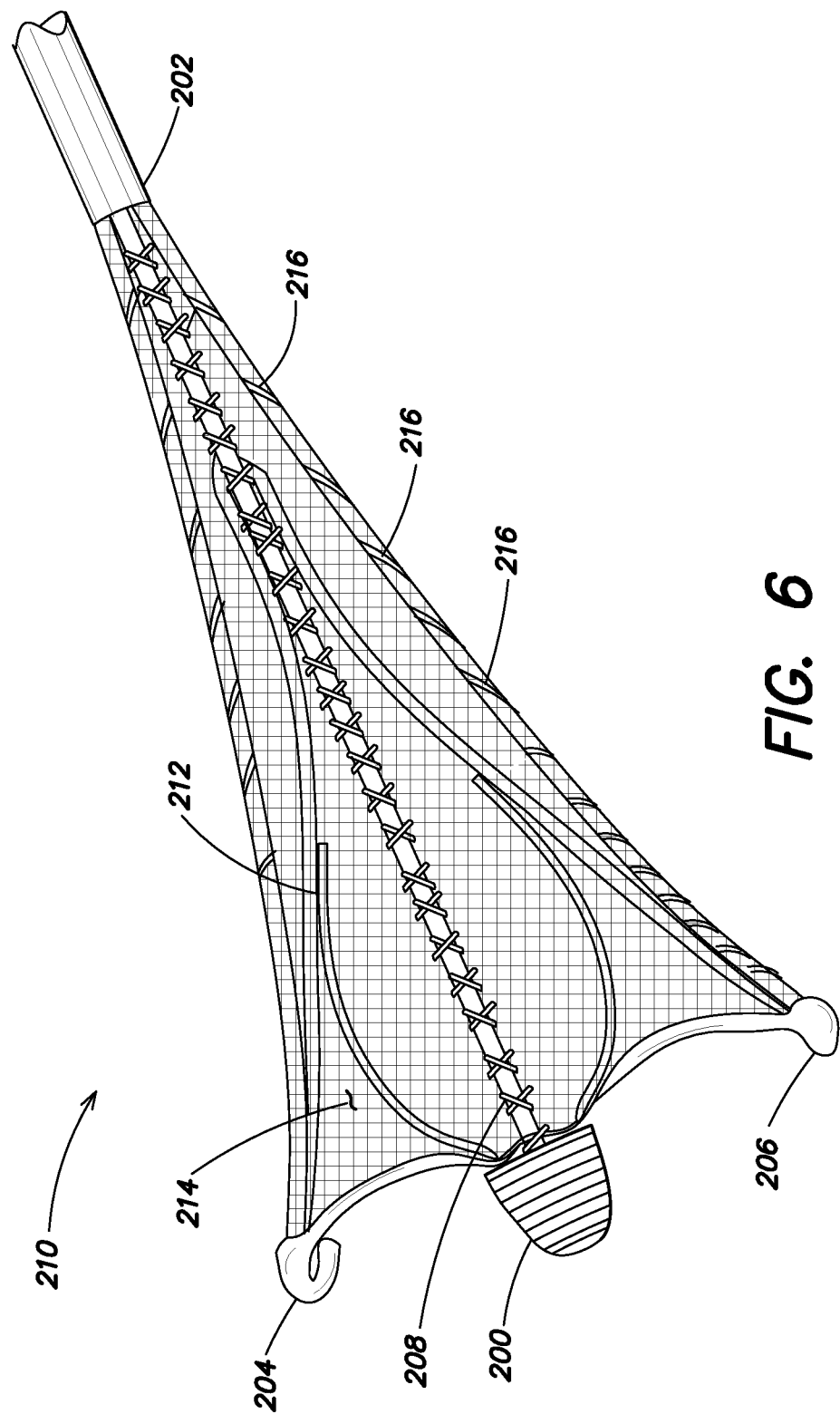

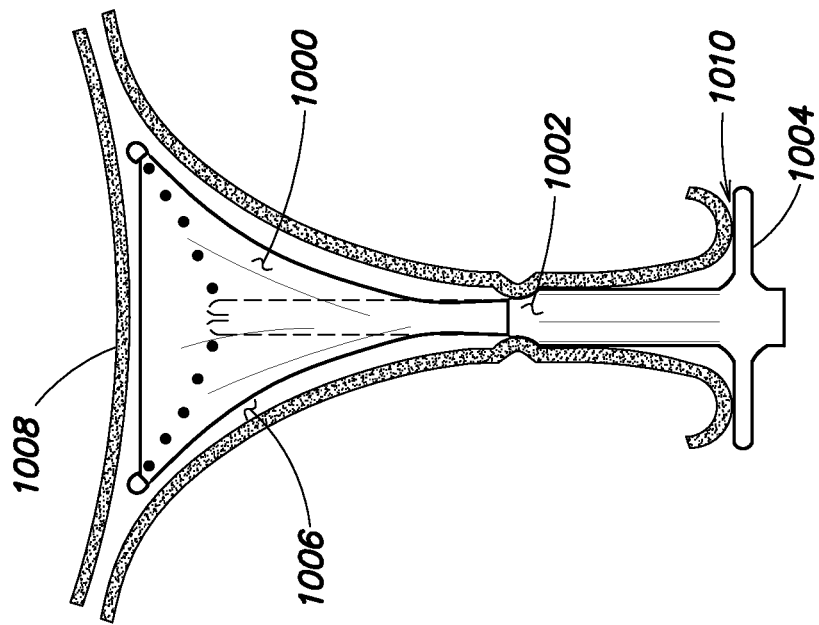
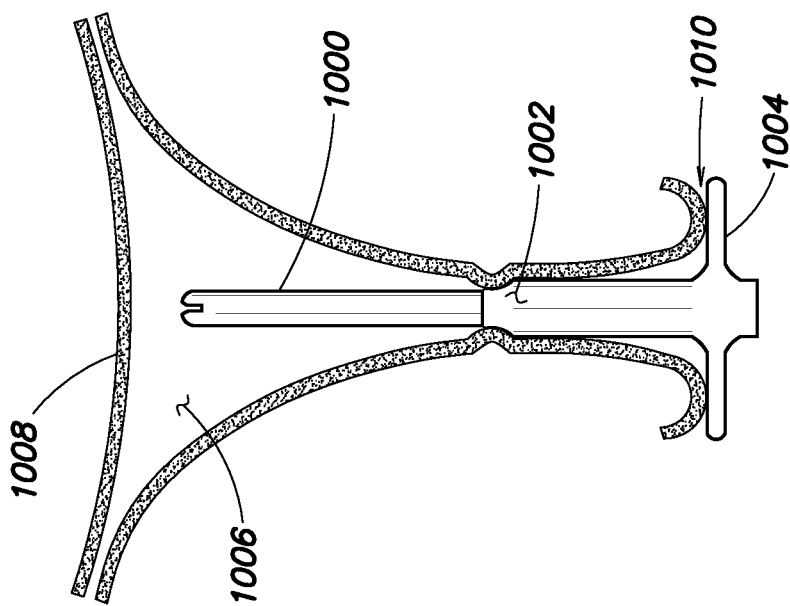
FIG. 19A
FIG. 19B ated under 35 U.S.C. § 120.

FUNDUS BUMPER MECHANICAL REFERENCE FOR EASIER MECHANISM DEPLOYMENT

RELATED APPLICATION DATA

This application is a continuation of pending U.S. Pat. No. 10,624,694, filed Mar. 9, 2016, which is a continuation of U.S. Pat. No. 9,333,111, filed Feb. 14, 2013, the priority of which is claimed under 35 U.S.C. § 120.

BACKGROUND

1. Field of the Invention

The present invention generally relates to intrauterine devices and methods of deployment thereof.

2. Description of Background

Intrauterine medical devices are often inserted through a patient's cervix and then expanded inside the patient's uterus. For example, a uterine ablation procedure may be performed by inserting a sheath through the cervix and then extending an applicator through the distal end of the sheath and expanding the applicator in the uterus. The applicator is expanded inside the patient, out of view of the person performing the procedure. Reliable and proper positioning and deployment of the applicator is important to avoid potential injury to the patient. Additionally, the applicator should reliably contract back into the sheath for removal from the patient.

SUMMARY OF INVENTION

Deployment of an intrauterine device in the uterine cavity may be a blind operation; for example, a physician may have no visual access to the uterine cavity. Typically, deployment of an intrauterine device is a multi-step, technique-sensitive task largely based on physician experience, thereby increasing the risk of injury to the patient. Accordingly, aspects and embodiments of the present disclosure are directed to providing intrauterine devices that may be deployed with ease, particularly during the seating of the device in the uterine cavity. Aspects and embodiments are also directed to providing methods for facilitating deployment of intrauterine devices within the uterine cavity.

According to one aspect, an intrauterine device includes a structure including a first central support member and a deployment mechanism coupled to the first central support member. The deployment mechanism may be configured to extend from a collapsed position substantially aligned with the first central support member to a deployed position flexing away from the first central support member. The intrauterine device further includes a second central support member that is different from the first central support member and is disposed substantially parallel to the first central support member. The intrauterine device further includes a bumper positioned at a distal end of the second central support member. The bumper may be arranged to be at a more distal position relative to a distal end of the structure so as to prevent the distal end of the structure from contacting a tissue of a uterus during deployment of the deployment mechanism. According to one embodiment, the tissue of the uterus of a patient may be a fundus tissue and the bumper may be configured to provide a mechanical positional reference to the fundus.

In some embodiments of the intrauterine device, the bumper may be arranged to be at a more distal position relative to the distal end of the structure in both the collapsed position and the deployed position of the deployment mechanism. In various embodiments, the bumper and the structure may be constructed and arranged so that a movement of the bumper is controllable independently from a movement of the structure. The movement of the bumper may be controlled using the second central support member.

In some embodiments, the first and second central support members may be configured to move relative to each other along a longitudinal direction of the first and second central support members so as to change a position of the bumper relative to the distal end of the structure along the longitudinal direction. The first and second central support members may be arranged in a telescoping configuration. In some embodiments, the bumper may be configured to move to a retracted position when the deployment mechanism is in a deployed position, the retracted position being one of a more proximal position than the distal end of the structure and a position that is substantially aligned with the distal end of the structure. Movement of the bumper to a retracted position is along a longitudinal direction of the central support members. In some embodiments, the structure may be configured to support a mesh array and the second central support member that is coupled to the bumper may be configured to move along the longitudinal direction within the mesh array.

In some embodiments, the deployment mechanism may be symmetric about the first and second central support members. The distal end of the structure may include a plurality of tips. The plurality of tips may be substantially aligned with the first and second central support members in the collapsed position of the deployment mechanism and may be displaced away from the first and second central support members in the deployed position of the deployment mechanism.

In some embodiments, the bumper may include a domed structure. The bumper may be made of a soft material. In various embodiments, the intrauterine device may be an ablation device and the bumper may be made of an electrically conductive material to facilitate ablation of the tissue of the uterus. For example, the bumper may include one or more of a porous material, a hydrophilic material, a conductive polymer and a material infused with an electrically conductive particulate.

According to some embodiments of the intrauterine device having a second support member coupled to the bumper, the bumper may include a thin flexible membrane disposed at least partially around the distal end of the structure in the collapsed position. The thin flexible membrane may be configured to at least one of retract and flatten in the deployed position so as to facilitate an approach of the structure to the tissue of the uterus in the deployed position. The thin flexible membrane may be configured to conform to the tissue of the uterus in the deployed position. The thin flexible membrane may be made of silicone. The thin flexible membrane may include one or more of a porous material, a hydrophilic material, a conductive polymer and a material infused with an electrically conductive particulate.

In some embodiments, the intrauterine device may further include a mechanical force gauge configured to provide a measure of a force experienced by the bumper. The intrauterine device may further be configured to limit the force.

According to another aspect, an intrauterine device includes a structure having a first central support member and a deployment mechanism coupled to the first central support member. The deployment mechanism may be configured to extend from a collapsed position substantially aligned with the first central support member to a deployed position flexing away from the first central support member. The intrauterine device further includes a bumper coupled to the deployment mechanism. The bumper may be configured to move from a more distal position relative to a distal end of the structure to a more proximal position relative to the distal end of the structure in response to extending the deployment mechanism from the collapsed position to the deployed position, so as to prevent the distal end of the structure from contacting a tissue of a uterus during deployment of the deployment mechanism. In some embodiments, the tissue may include a fundus of the uterus and the bumper may be configured to provide a mechanical positional reference to the fundus.

In some embodiments of the intrauterine device, the bumper may be a flexible ribbon coupled to the deployment mechanism. The ribbon may be substantially aligned with the first central support member in the collapsed position of the deployment mechanism. The ribbon may further be configured to substantially flatten along a direction substantially perpendicular to the first central support member in the deployed position of the deployment mechanism so as to allow the structure to contact the tissue of the uterus in the deployed position.

In some embodiments of the intrauterine device, the bumper coupled to the deployment mechanism may be a thin flexible membrane disposed at least partially around the distal end of the structure in the collapsed position of the deployment mechanism. The thin flexible membrane may be configured to at least one of retract and flatten in the deployed position of the deployment mechanism so as to facilitate an approach of the structure to the tissue of the uterus in the deployed position. The thin flexible membrane may be configured to conform to the tissue of the uterus in the deployed position. The thin flexible membrane may be made of silicone. The thin flexible membrane may include one or more of a porous material, a hydrophilic material, a conductive polymer and a material infused with an electrically conductive particulate.

In some embodiments of the intrauterine device having a bumper coupled to the deployment mechanism, the deployment mechanism may be symmetric about the first central support member. The structure including the deployment mechanism may further be configured to support a mesh array. The distal end of the structure may include a plurality of tips. The tips may be the tips of the mesh array. The plurality of tips may be substantially aligned with the first central support member in the collapsed position of the deployment mechanism and may be displaced away from the first central support member in the deployed position of the deployment mechanism.

In some embodiments of the intrauterine device having a bumper coupled to the deployment mechanism, the intrauterine device may further include a mechanical force gauge configured to provide a measure of a force experienced by the bumper. The intrauterine device may further be configured to limit the force.

According to another aspect, a method for facilitating deployment of a deployment mechanism of an intrauterine device may be provided. The method may include acts of positioning a bumper of the intrauterine device at a more distal position relative to a distal end of the deployment mechanism; advancing the mechanism into a uterus such that the bumper contacts a fundus of the uterus; and extending the deployment mechanism from a collapsed position substantially aligned with a first central support member of the intrauterine device to a deployed position flexing away from the first central support member, the bumper preventing the distal end of the deployment mechanism from contacting the fundus during deployment of the deployment mechanism. In some embodiments, the method may further include an act of advancing the deployment mechanism relative to the bumper in the deployed position. Advancing the deployment mechanism relative to the bumper may further include positioning the deployment mechanism such that the mechanism contacts the fundus. In some embodiments, the acts of advancing the mechanism into a uterus such that the bumper contacts a fundus of the uterus and extending the mechanism may overlap at least partially. In some embodiments, the method may further include an act of flattening the bumper substantially simultaneously with extending the deployment mechanism such that the deployment mechanism contacts the fundus in the deployed position.

According to another embodiment, a method for facilitating deployment of a structure including a deployment mechanism and a first central support member of an intrauterine device using a bumper configured to be at a more distal position relative to a distal end of the structure with the deployment mechanism in a collapsed state may comprise acts of advancing the structure with the deployment mechanism in the collapsed state through a cervix canal and into a uterus of a patient such that the bumper contacts a fundus of the uterus in the collapsed state; deploying the deployment mechanism from the collapsed state to a deployed state flexing away from the first central support member so that the bumper prevents the distal end of the structure from contacting the fundus during deployment of the deployment mechanism; and causing the deployment mechanism and the bumper to move relative to each other. In some embodiments, the method may further comprise an act of further advancing the structure in the deployed state so as to be closer to the fundus while the bumper maintains contact with the fundus.

In some embodiments, the acts of deploying the deployment mechanism and causing the deployment mechanism and the bumper to move relative to each other may overlap at least partially. The act of causing the deployment mechanism and the bumper to move relative to each other may comprise flattening the bumper such that the bumper is aligned substantially with the distal end of the structure. The act of causing the deployment mechanism and the bumper to move relative to each other may comprise telescoping a second central support member attached to the bumper within the first central support member.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures:

FIG. 6 is a perspective view of the embodiment in FIG. 4, illustrating the deployment mechanism advanced closer to the bumper according to aspects of the present invention;

FIG. 19A illustrates an exemplary embodiment of a portion of an intrauterine device having a flange and seated in the uterus in a collapsed position according to aspects of the present invention;

FIG. 19B illustrates the portion of the intrauterine device of FIG. 19A in a deployed position according to aspects of the present invention.

DETAILED DESCRIPTION

Figure 1:
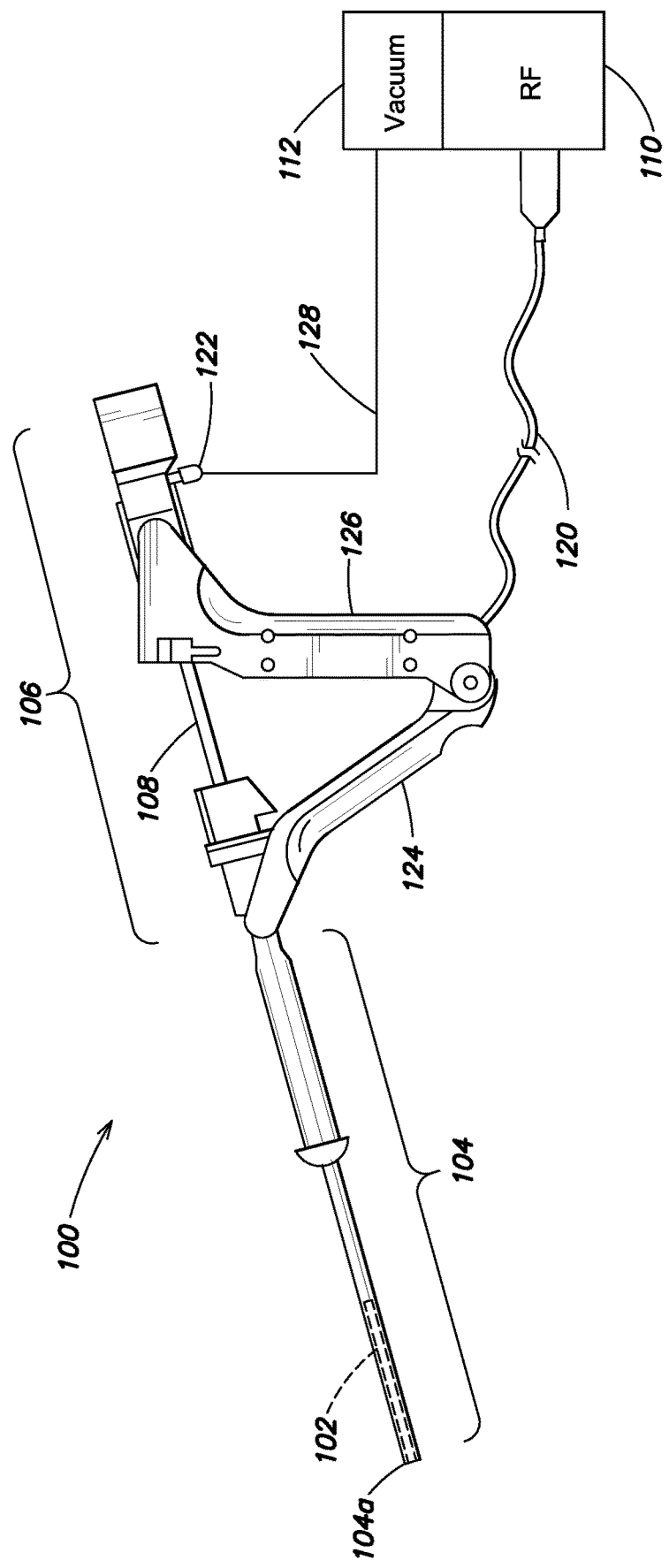
FIG. 1 is a side elevation view of an intrauterine device with an applicator in a retracted position according to aspects of the present invention.

Aspects and embodiments of this disclosure are directed to providing various structures and methods for convenient and safe deployment of an intrauterine device. The intrauterine device may be an intrauterine therapy application device including a deployment mechanism that may be deployed within the uterus of a patient.

Deploying a deployment mechanism of an intrauterine device may include advancing the deployment mechanism to the fundus of the uterus and expanding the deployment mechanism by repeatedly sliding the device proximally and distally about 0.5 cm as the deployment mechanism is expanded from a collapsed position to a deployed position, lightly tapping against the fundus on each proximal stroke. Repeatedly sliding the device back and forth prevents at least a portion of the deployment mechanism, such as the tips disposed at a distal end of the deployment mechanism, from being buried in the fundus tissue while the deployment mechanism is expanding. However, this method relies on skillful manipulation of the device and repeated tapping against the fundus tissue during deployment of the mechanism, which may be inconvenient and uncomfortable to the patient and may result in increased risk of injury to the patient if a portion of the deployment mechanism becomes buried in the fundus tissue during deployment due to unskillful manipulation.

According to one aspect of the present disclosure, convenient and safe deployment is achieved by providing an intrauterine device including a bumper. The bumper may be disposed at a distal end of the intrauterine device. The bumper may be configured to prevent at least a portion of the deployment mechanism of the intrauterine device from being buried in a tissue of the uterus during deployment. In some embodiments, the bumper may be a fundus bumper. The fundus bumper may be configured to provide a mechanical positional reference to the fundus.

According to another aspect of the present disclosure, convenient and safe operation of an intrauterine device is achieved by providing methods of facilitating the deployment of a mechanism of the intrauterine device. In some embodiments, a method of facilitating deployment may include positioning a bumper of the intrauterine device at a more distal position relative to the deployment mechanism. The method may further include advancing the deployment mechanism until the bumper contacts the fundus. The method may further include expanding the deployment mechanism and preventing the deployment mechanism from contacting the fundus during deployment using the bumper. One advantage of this method is that it prevents the deployment mechanism from becoming buried in the fundus tissue without requiring the above-described user manipulation, including repeated tapping against the fundus tissue during deployment of the deployment mechanism, thereby allowing convenient and safe deployment of the mechanism.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Referring to the Figures, illustrated in FIG. 1 is an intrauterine therapy application device 100 including an applicator 102, a sheath 104, and an RF generator 110. As used herein, the terms applicator, applicator structure and structure may be used interchangeably and may refer to a structure of the applicator. According to one embodiment, the sheath is inserted through the patient's cervix. The applicator may be retracted in a collapsed position within the sheath for insertion into the patient's cervix, as shown in the exemplary embodiment of FIG. 3. As shown in FIG. 1, the applicator 102 is in a retracted position inside the hollow sheath 104. The sheath may be inserted through the patient's cervix, and when the distal end 104a of the intrauterine therapy application device 100 is inside the uterus, the applicator may be extended into the uterus in a collapsed position, and expanded into a deployed state in the uterus, as shown in the exemplary embodiment of FIG. 4 and discussed further below.

The intrauterine therapy application device 100 includes a handle 106, and is coupled via a cable 120 to a radiofrequency signal generator 110 and via a tube 128 to a vacuum source 112. The radiofrequency generator 110 generates an electrical signal, for example a radiofrequency signal, and transmits it to the applicator 102 through the cable 120, which is ultimately coupled to the applicator through the handle 106. The vacuum source 112 is connected to the handle 106 at the vacuum port 122 and creates suction in the distal end of the applicator 102.

Figure 2:
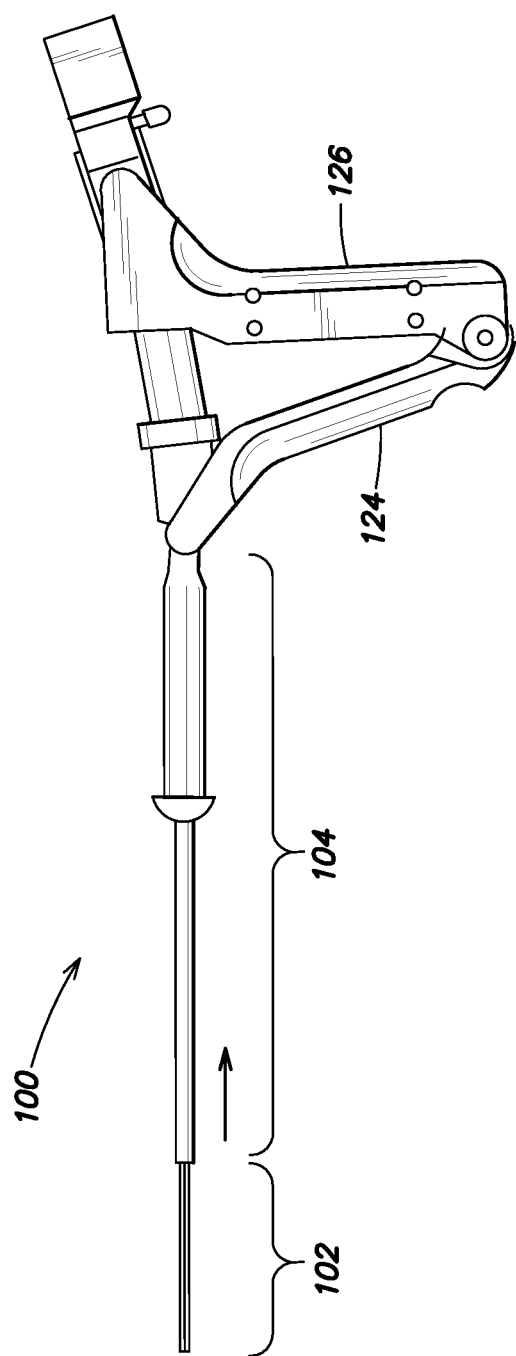
FIG. 2 is a side elevation view of the intrauterine device of FIG. 1, showing the applicator in an extended position according to aspects of the present invention.

The handle 106 includes a distal grip 124 and a proximal grip 126. During use, the proximal grip 126 is squeezed toward the distal grip 124, to cause the applicator 102 to extend out from the sheath 104, as shown in FIG. 2. As shown in FIG. 2, the applicator 102 is extended out from the sheath 104 in a collapsed position. In some embodiments, as the applicator 102 extends out from the sheath 104 in the collapsed position, it may also expand as shown in the perspective view of the deployed applicator illustrated in FIG. 4.

According to one feature, the distal end 104a of the intrauterine therapy application device 100 is configured to be inserted into a patient's cervix. The distal end 104a includes a bumper according to aspects of the present disclosure. The bumper is configured to prevent a distal end of the applicator 102 from becoming buried in cervical tissue, such as the fundus tissue, as the applicator 102 is expanded from a collapsed position to a deployed position.

Figure 3:
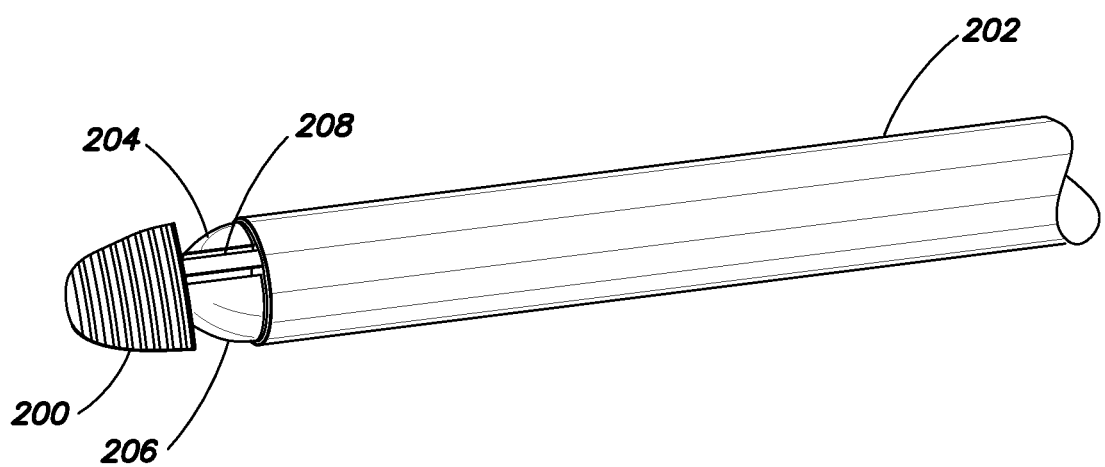
FIG. 3 is a perspective view of a portion of one embodiment of an intrauterine device in a collapsed position according to aspects of the present invention.

FIG. 3 is a perspective view of a portion of one embodiment of an intrauterine device, including a bumper 200. The bumper 200 is disposed at the distal end of the intrauterine device. In one example, the intrauterine device may be the intrauterine therapy application device 100 in FIG. 1. The intrauterine device further includes a sheath 202. The sheath is a hollow tube configured to house an applicator in a collapsed position. The applicator is retracted into the sheath 202 in a collapsed position and therefore is not visible in FIG. 3. The applicator includes tips 204 and 206 disposed at the distal end of the applicator. When the applicator is in a collapsed position as shown, the bumper 200 is disposed at the distal end of the intrauterine device, which is at a more distal position relative to the tips 204 and 206. This allows the applicator to be deployed within the uterus of a patient without the risk of burying the tips 204 and 206 in uterine tissue, such as the fundus tissue.

The bumper 200 is coupled to a central support member 208. In the collapsed position of the applicator, each of the tips 204 and 206 is substantially aligned along a longitudinal direction of the central support member 208. The central support member 208 may be controlled independently from the applicator. For example, the applicator may have a separate central support member configured to slide through the sheath 202 to extend and retract the applicator. In the collapsed position, the tips 204 and 206 do not extend beyond the bumper 200. The central support member 208 may be configured to slide through the sheath 202, thereby moving the bumper relative to the tips 204 and 206.

Figure 4:
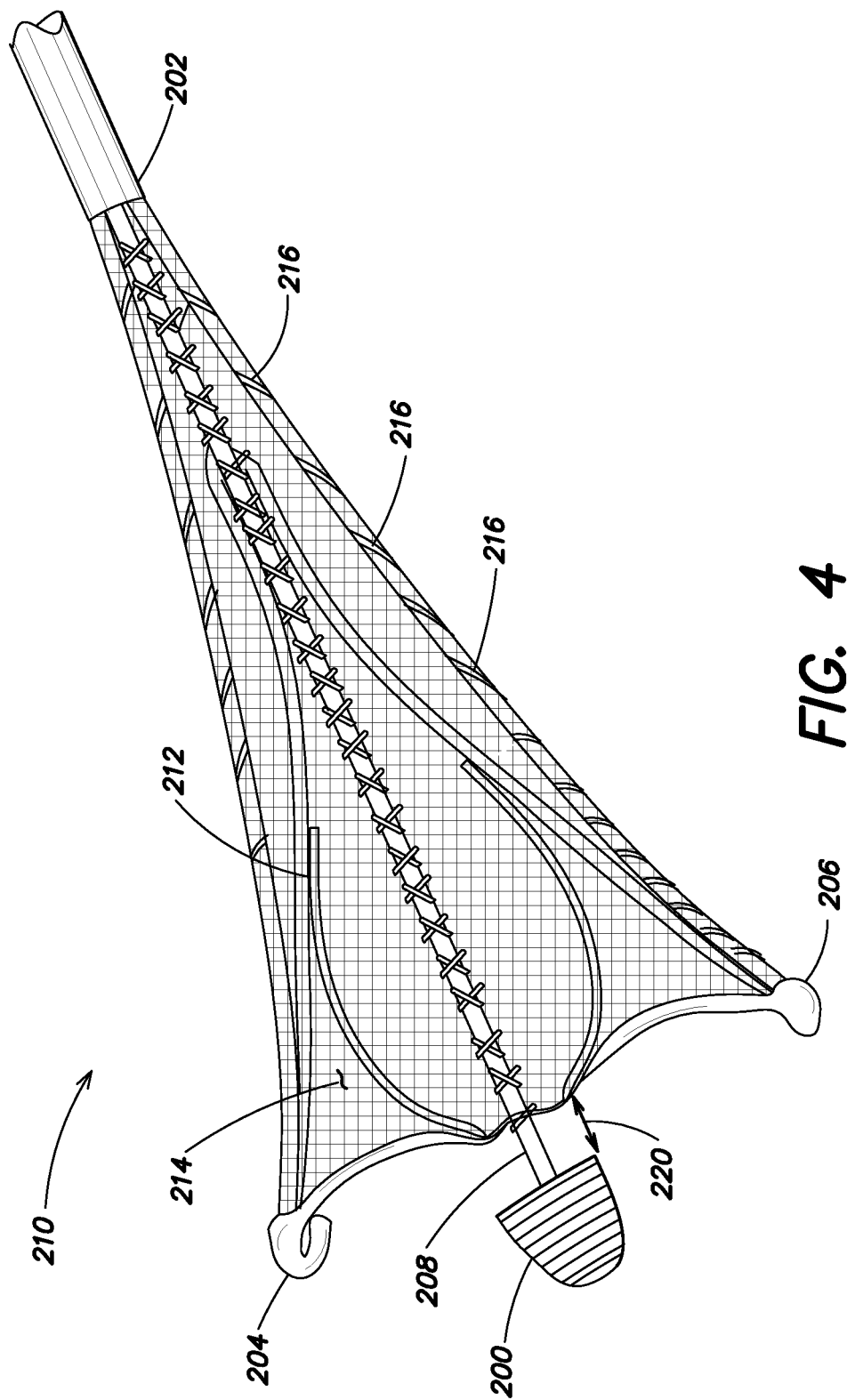
FIG. 4 is a perspective view of the portion of the intrauterine device of FIG. 3 in a deployed position according to aspects of the present invention.

FIG. 4 is a perspective view of the portion of the intrauterine device of FIG. 3, including the sheath 202 and the bumper 200 disposed at the distal end of the central support member 208. FIG. 4 further illustrates the structure of the applicator 210 in a deployed position. The applicator 210 includes a deployment mechanism 212, a mesh array 214 and tips 204 and 206 disposed at the distal end of the applicator. The deployment mechanism 212 is coupled to a central support member (not shown) that is included in the applicator structure and is separate from the central support member 208 of the bumper 200. The central support member that is coupled to the deployment mechanism 212 is a first central support member and the central support member 208 coupled to the bumper 200 is a second central support member that is different from the first central support member. The first and second central support members are substantially parallel and configured to slide through the sheath 202. The first and second central support members may be arranged in a telescoping configuration. The deployment mechanism 212 is configured to expand the applicator 210 from a collapsed position that is substantially parallel to the central support members to a deployed position flexing away from the central support members as shown in FIG. 4.

The mesh array 214 surrounds the applicator 210. The mesh array 214 may be knitted from a nylon and spandex knit and plated with gold, silver, or another conductive material. The mesh array 214 may be configured to be conformable, permeable, and to carry current. The mesh array 214 may be attached to at least a portion of the deployment mechanism 212, such as external flexures of the deployment mechanism 212, with strands of thread 216, as shown in FIG. 4. The strands of thread may be nylon. The strands of thread may be sewn through the mesh array 214 and around the external flexures. Some examples of a mesh array are described in U.S. Pat. No. 6,813,520 to Truckai et al., which is hereby incorporated by reference herein in its entirety.

Figure 5:
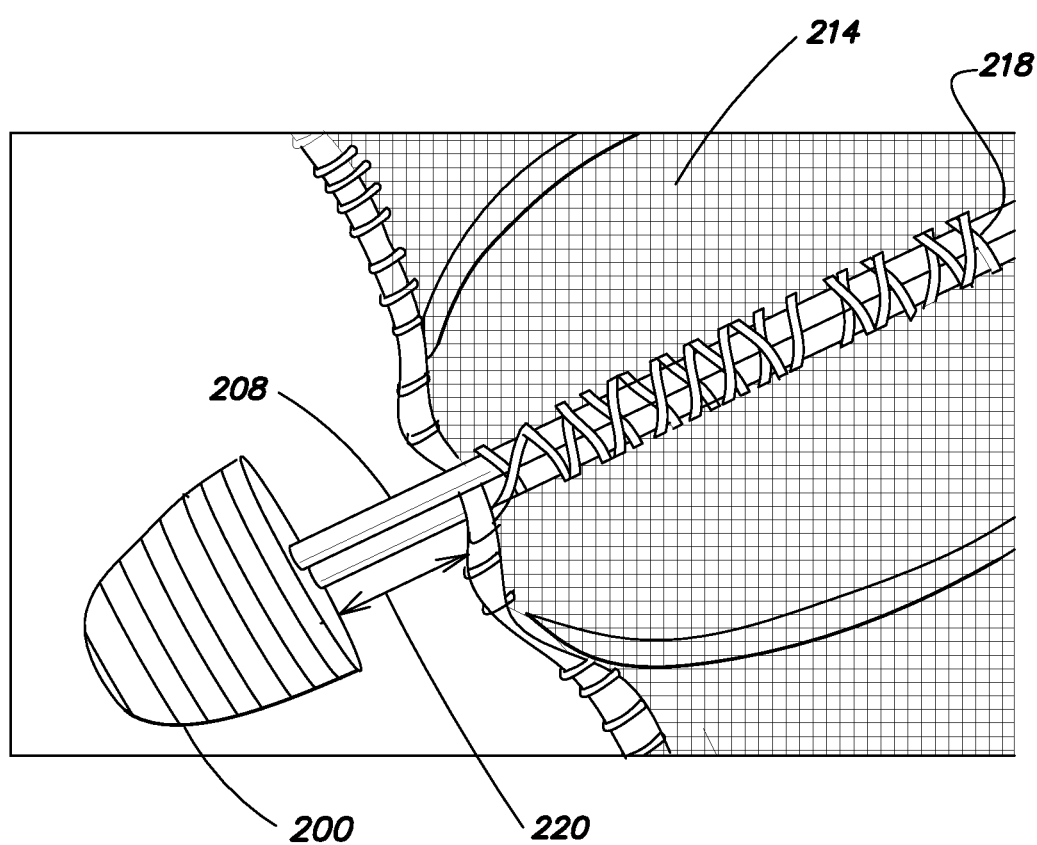
FIG. 5 is a magnified view of a portion of the embodiment in FIG. 4.

FIG. 5 shows a magnified view of a portion of the mesh array 214 of FIG. 4. The mesh array 214 may be configured to allow the central support member 208 to slide through the mesh array. For example, as shown in FIG. 5, portions of the mesh array 214 may be held together using strands of thread 218 sewn around the central support member 208. The strands of thread 218 may be sewn loosely around the central support member 208 to reduce friction between the mesh array 214 and the central support member. In some embodiments, the bumper 200 may be coupled to a plurality of central support members. In some embodiments, the central support member 208 may include two rods as shown in FIG. 5, which are rigidly mechanically coupled to the proximal section of the intrauterine device. The coupling rods are woven through the center stripe of the mesh array 214 to help center the bumper.

Referring again to FIG. 4, as the applicator structure 210 deploys, the tips 204 and 206 shift away from the central support member 208, thereby leaving a gap 220 between the bumper 200 and the applicator structure in a longitudinal direction along the central support member. During deployment of the deployment mechanism, the bumper 200 remains at a more distal position relative to the tips 204 and 206, guaranteeing that the bumper is resting against the fundus and that the tips do not engage the fundus during deployment. Following deployment of the deployment mechanism, the bumper 200 may also remain at a more distal position relative to the tips 204 and 206. The bumper 200 may further be configured to move relative to the tips 204 and 206 following deployment of the deployment mechanism. The central support members of each of the applicator structure 210 and the bumper 200 may be configured to slide against each other in the longitudinal direction, thereby eliminating the gap 220 as shown in FIG. 6. The deployment mechanism 212 is advanced closer to the bumper 200 in FIG. 6. As a result, the mesh array 214 may approach the uterine tissue after the deployment mechanism is deployed, allowing better contact between the applicator structure 210 and the uterine tissue. In the retracted position of the bumper 200 shown in FIG. 6, the bumper is substantially aligned with the distal end (tips 204, 206) of the applicator structure 210. In some embodiments, the bumper may be configured to further move to a retracted position that is a more proximal position relative to the distal end (tips 204, 206) of the applicator structure 210 in the deployed position.

In the embodiments illustrated in FIGS. 4-6, the applicator structure 210 is substantially symmetric around the central support member. However, other embodiments may include other configurations of the applicator structure, such as asymmetric configurations around a central support member of the intrauterine device. The central support member may be coupled to a centrally positioned bumper, allowing the bumper to contact the fundus.

The bumper may be configured to be inserted into a patient's cervix. The bumper may include a domed end or structure. The bumper may be domed or rounded to mimic the tip of a dilator, facilitating smooth insertion. The bumper may be made of a soft material. In other embodiments, the bumper may be made of rigid materials such as rigid plastic.

Exemplary processes for operation of various embodiments of an intrauterine device having a bumper are illustrated and described with reference to FIGS. 7A to 7B and FIGS. 8A to 8C. These exemplary processes may be applied using various embodiments of intrauterine devices.

Figure 7B:
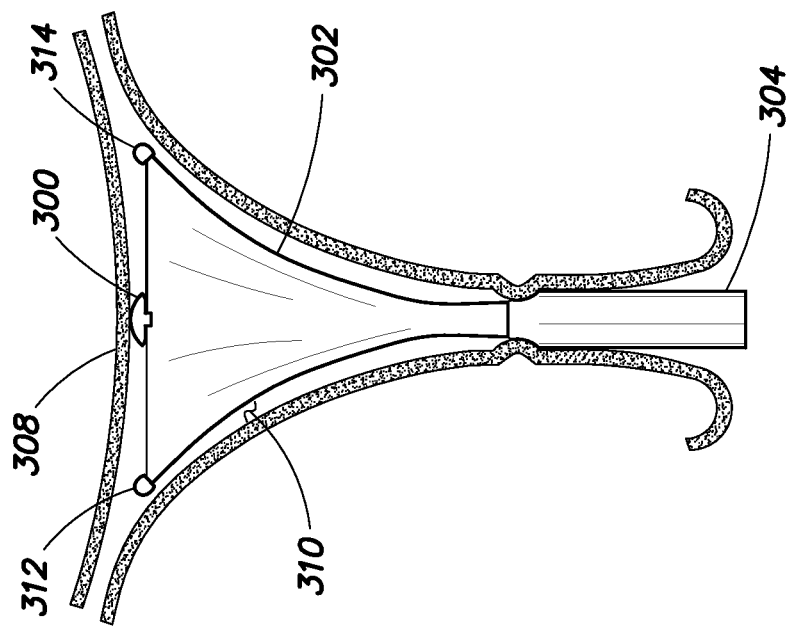
FIG. 7B illustrates an exemplary embodiment of a portion of the intrauterine device of FIG. 7A in a deployed position according to aspects of the present invention.
Figure 7A:
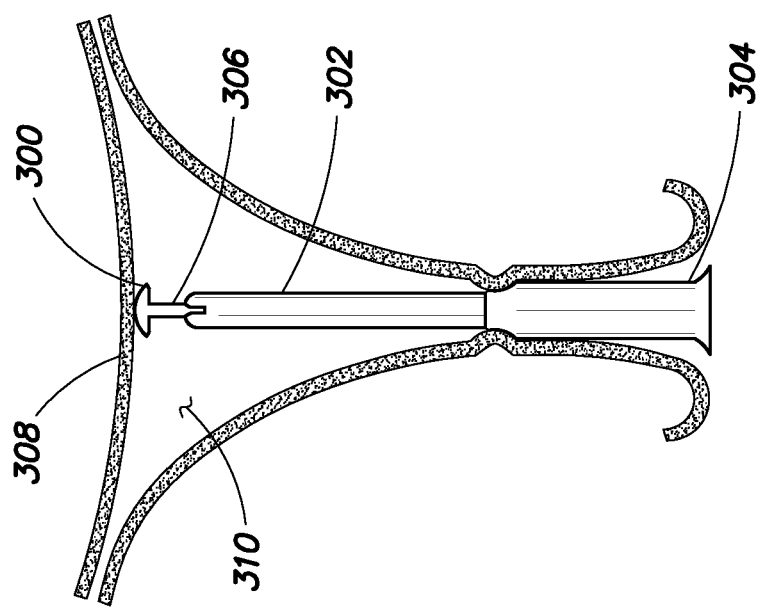
FIG. 7A illustrates an exemplary embodiment of a portion of an intrauterine device seated in the uterus in a collapsed position according to aspects of the present invention.

FIG. 7A illustrates one embodiment of a portion of an intrauterine device seated in a uterus in a collapsed position. In one example, the intrauterine device may be the embodiment described with reference to FIGS. 3 to 6. The intrauterine device includes a bumper 300 disposed at the distal end of the device and contacting the fundus 308 of the uterus 310. The intrauterine device further includes an applicator structure 302 extending through a sheath 304 into the uterus 310. A central support member 306 coupled to the bumper 300 may be used to control the position of the bumper. As shown in FIG. 7A, the bumper 300 may be positioned so as to leave a gap between the bumper and a distal end of the applicator structure 302, to prevent at least a portion of the applicator structure 302 from contacting the fundus 308. In other embodiments, a gap between the bumper and the distal end of the applicator structure may be reduced or eliminated in the collapsed position, as shown for example in FIG. 3.

FIG. 7B illustrates the embodiment of FIG. 7A in a deployed position. As the applicator structure 302 is deployed, the bumper 300 remains in contact with the fundus 308 and may contact the applicator structure. The tips 312 and 314 of the applicator structure 302 do not contact the fundus 308 during deployment due to the presence of the bumper 300. The applicator structure may include a deployment mechanism and a mesh array as described earlier and the tips 312 and 314 may be array tips.

Figure 8A:
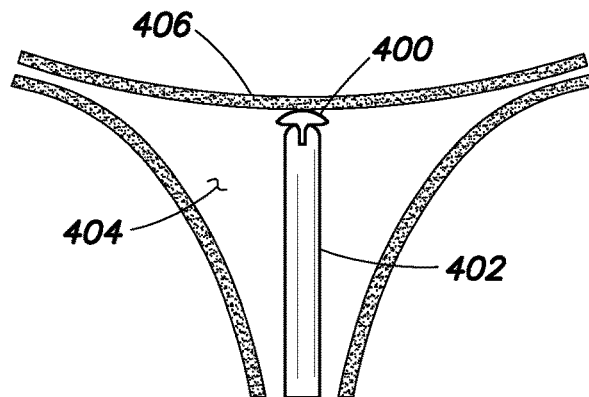
FIG. 8A illustrates an exemplary embodiment of a portion of an intrauterine device seated in the uterus in a collapsed position according to aspects of the present invention.
Figure 8B:
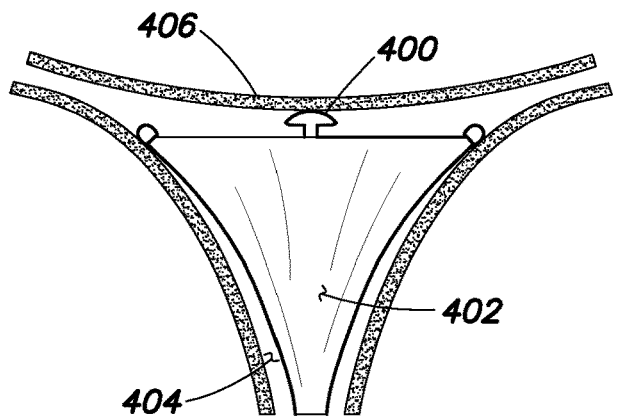
FIG. 8B illustrates an exemplary embodiment of a portion of the intrauterine device of FIG. 8A in a deployed position according to aspects of the present invention.
Figure 8C:
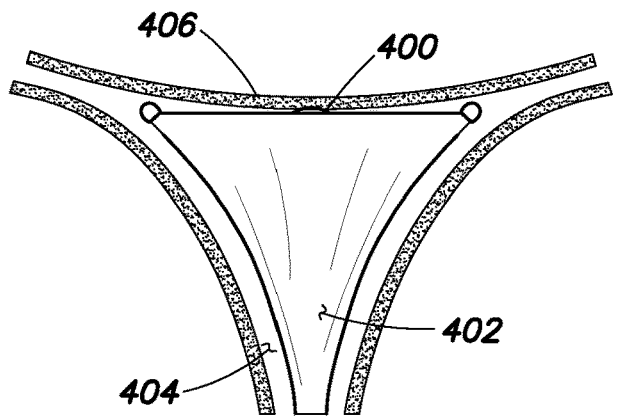
FIG. 8C illustrates an exemplary embodiment of a portion of the intrauterine device of FIG. 8B, with the deployed mechanism advanced closer to the bumper according to aspects of the present invention.

FIG. 8A illustrates one embodiment of a portion of an intrauterine device seated in a uterus in a collapsed position. In one example, the intrauterine device may be the embodiment described with reference to FIGS. 3 to 6. The intrauterine device includes a bumper 400 and an applicator structure 402 positioned within the uterus 404 such that the bumper contacts the fundus 406. The bumper 400 is also configured to contact the distal end of the applicator structure 402 in the collapsed position. FIG. 8B illustrates the embodiment of FIG. 8A in a deployed position. As the applicator structure 402 is deployed, the bumper 400 prevents the applicator structure from contacting the fundus 406. In the deployed position, there may be a gap between the bumper 400 and the deployed applicator structure 402, which may be reduced or eliminated by advancing the applicator structure towards the bumper, as shown in FIG. 8C. In some embodiments, the applicator structure 402 may be deployed while advancing the applicator structure towards the bumper 400, such that when the applicator structure is completely deployed, it contacts the bumper.

As illustrated in the embodiments of FIGS. 7A-7B and 8A-8C, the bumper remains a stationary reference at the fundus while the applicator structure deploys. The intrauterine device may be configured such that movement of the bumper may be controlled independently of the movement of the applicator structure. In some embodiments, the intrauterine device may be configured to control the motion of the bumper and array tips of the applicator structure relative to each other. In some embodiments, the intrauterine device may include a disposable hand piece configured to control the motion of the bumper and the deployment mechanism of the applicator.

According to an aspect of the present disclosure, it may be best for the bumper to take up as little space as possible following deployment of the applicator structure, so as not to prevent intimate contact between the applicator and the fundus.

Figure 9A:
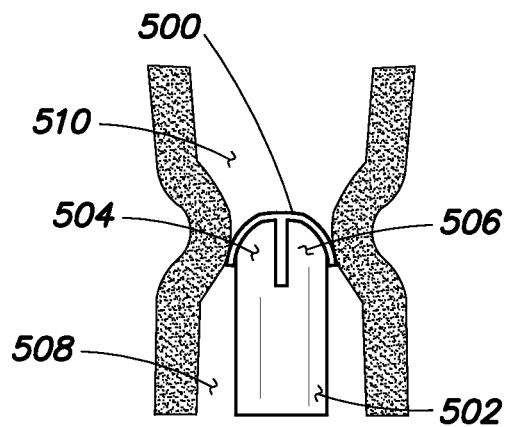
FIG. 9A illustrates a schematic view of an exemplary embodiment of a flexible thin membrane bumper disposed around a distal end of an intrauterine device according to aspects of the present invention.

FIG. 9A illustrates an exemplary embodiment of a flexible thin membrane bumper disposed around a distal end of an intrauterine device. The bumper 500 is thin and flexible and is positioned on, but not fixed to, the rounded tips 504 and 506 of the applicator structure 502, thereby providing a rounded dilator profile. The bumper 500 and the tips 504 and 506 are configured to mimic a dilator as the device passes through the cervical canal 508 into the uterus 510. In some embodiments, the flexible thin membrane bumper may be flat in the resting state. While being passed through the cervical canal, the bumper may be soft enough to fold over the tips, taking more of a domed shape. In other embodiments, the flexible thin membrane bumper may be rounded in the resting state.

In some embodiments, the flexible thin membrane bumper may be coupled to a second central support member that is separate from a first central support member, as shown for example in FIG. 4, wherein the first central support member is coupled to a deployment mechanism of the intrauterine device. The second central support member may be controlled independently from the first central support member. In other embodiments, an intrauterine device having a flexible thin membrane bumper may not include a second central support member. In these embodiments, the flexible thin membrane bumper may be coupled to at least a portion of a deployment mechanism of the intrauterine device and may further be configured to retract from a more distal position compared to a distal end of the applicator structure 502 (such as more distal than the tips 504, 506 as shown in FIG. 9A) to a more proximal position compared to the distal end of the applicator structure 502 (such as more proximal than the tips 504, 506 as shown in FIG. 9B) during deployment of the deployment mechanism of the applicator structure.

In some embodiments, the bumper 500 may be made of silicone. As the applicator structure 502 is deployed, the material of the bumper 500 may be flexible enough to easily flatten, allowing a portion of the applicator structure, such as a mesh array, to make good contact with the fundus. Establishing good contact between the mesh array and the fundus allows for better application of therapy to the fundus tissue.

Figure 9B:
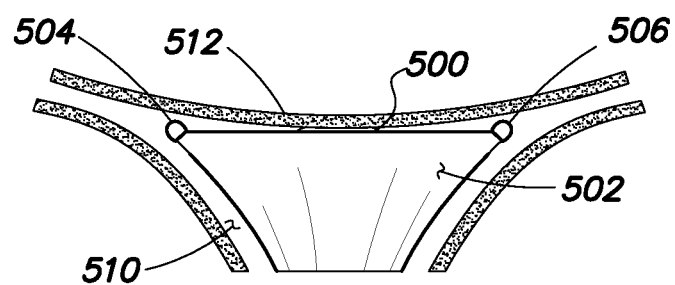
FIG. 9B illustrates the flexible thin membrane bumper of FIG. 9A being flattened in response to deploying the intrauterine device according to aspects of the present invention.

FIG. 9B illustrates the flexible thin membrane bumper 500 of FIG. 9A being retracted and flattened in response to deploying the applicator structure 502 within the uterus 510. The flexible thin membrane bumper 500 flattens as the tips 504 and 506 of the applicator structure 502 are spread apart during deployment. The bumper 500 is configured to conform to the fundus 512, facilitating improved contact between the mesh array of the applicator structure 502 and the fundus. In the deployed position, the bumper 500 may be retracted to a more proximal position relative to a distal end (tips 504, 506) of the applicator structure 502.

In some embodiments, the intrauterine device may be an ablation device. The bumper may be configured to allow electrical conductivity through the bumper, to ensure that it does not act as an insulator and locally prevent ablation of uterine tissue. In various embodiments, the bumper may be made of or may include one or more of a porous material, a hydrophilic material, a conductive polymer and a material infused with an electrically conductive particulate.

In some embodiments, an intrauterine device having a bumper according to aspects disclosed herein may further include a mechanical force gauge. The mechanical force gauge may used in conjunction with the bumper. A mechanical indicator, such as a scale or a dial, may be included in the device, for example, to provide a physician with a measure of the force experienced by the bumper. In one example, rather than reporting a force value, a colored go/no-go indicator may be provided. One advantage of a mechanical force gauge is to alert a physician if they were pressing too hard against the fundus. In some embodiments, the intrauterine device may further be configured to limit the axial force that a physician could apply to the bumper, thereby reducing the risk of excessive loading and risk of injury to a patient.

According to an aspect of the present disclosure, an intrauterine device including a deployment mechanism may further include a bumper that is coupled to the deployment mechanism. The movement of the bumper may be coupled to the deployment of the mechanism. In one embodiment, as the mechanism is deployed from a collapsed position to a deployed position, the bumper moves from a more distal position to a more proximal position compared to a distal end of the intrauterine device, wherein the movement of the bumper from a more distal position to a more proximal position is along a longitudinal direction of a first central support member that is coupled to the deployment mechanism. One embodiment of an intrauterine device including a bumper coupled to the deployment mechanism was described in relation to FIGS. 9A and 9B, wherein the flexible thin membrane bumper may be coupled to the deployment mechanism.

Figure 10A:
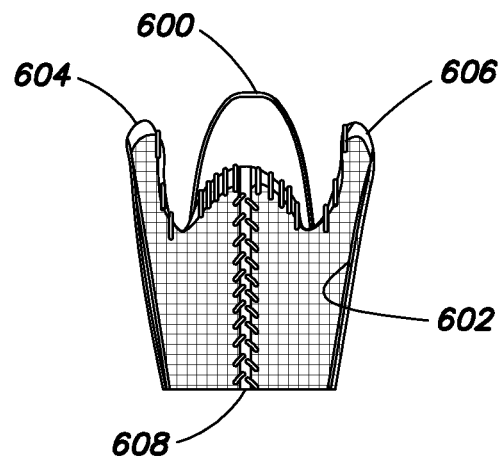
FIG. 10A illustrates an exemplary embodiment of a portion of an intrauterine device in a partially collapsed state according to aspects of the present invention.

FIG. 10A illustrates another embodiment including a bumper 600 coupled to a deployment mechanism 602 of an intrauterine device. The bumper 600 is configured as a ribbon with each end of the ribbon coupled to the deployment mechanism 602. The center of the ribbon is aligned with a central support member of the intrauterine device and the ends of the ribbon are coupled to the deployment mechanism at symmetric locations positioned on either side of the central support member. In some embodiments, the ribbon may be made of stainless steel. The ribbon may be welded to internal flexures of the deployment mechanism 602. The deployment mechanism 602 is configured to support or include a mesh array. The deployment mechanism 602 is a part of an overall applicator structure of the intrauterine device, as previously described. The applicator structure also includes the tips 604 and 606. In other embodiments, the deployment mechanism 602 may include the tips 604 and 606.

In FIG. 10A, the deployment mechanism 602 is shown to be partially deployed, with the bumper 600 being positioned at the distal end of the intrauterine device, thereby preventing a distal end of the applicator structure, such as the tips 604 and 606, from contacting the fundus tissue. The bumper 600 is configured to contact the fundus when the deployment mechanism 602 is in a collapsed position and to provide a mechanical positional reference to the fundus.

Figure 10B:
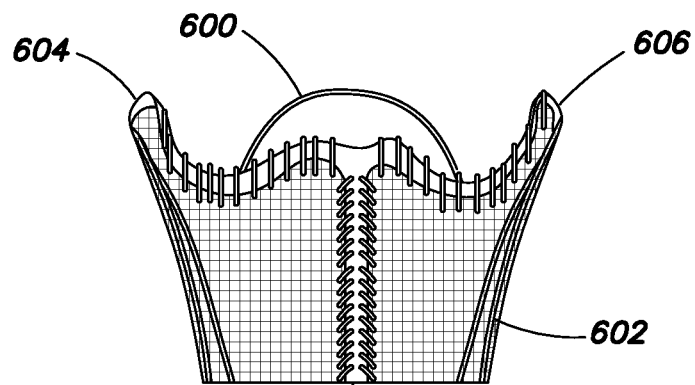
FIG. 10B illustrates an exemplary embodiment of a portion of the intrauterine device of FIG. 10A in a partially deployed state according to aspects of the present invention.
Figure 10C:
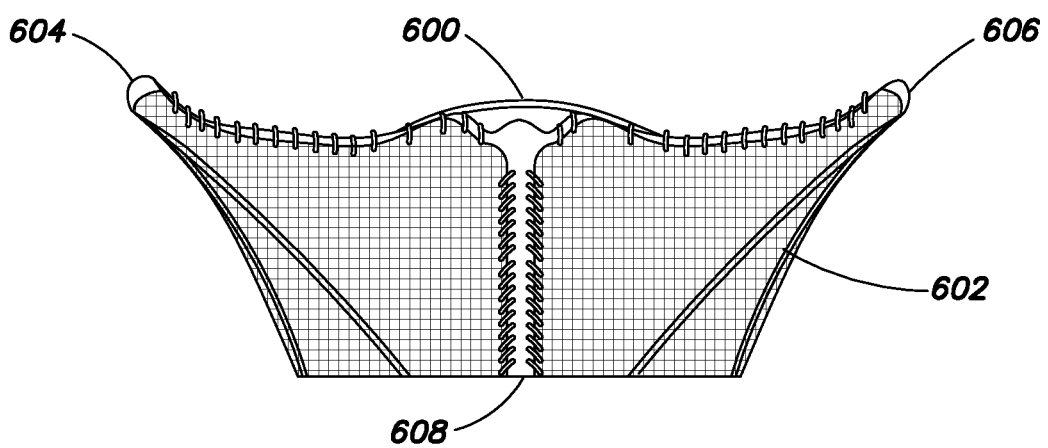
FIG. 10C illustrates an exemplary embodiment of a portion of the intrauterine device of FIG. 10A in a deployed position according to aspects of the present invention.

As the deployment mechanism 602 extends from a collapsed position to a deployed position, the tips 604 and 606 spread apart from each other and the bumper 600 gradually retracts as shown in FIGS. 10B and 10C. This configuration of the bumper 600 prevents the tips 604 and 606 from becoming buried in the fundus during deployment, while allowing the applicator structure to contact the fundus in the deployed position in order to enhance effectiveness of the therapy application. As the deployment mechanism 602 expands, the shape of the ribbon bumper 600 is altered. The ribbon's length and stiffness may be selected to allow the ribbon to protrude ahead of the tips 604 and 606 while the device is collapsed, and to gradually retract as the tips spread.

The ribbon bumper 600 may be made of a flexible material. In the collapsed position of the deployment mechanism 602, the ribbon may be collapsed or folded such that it is substantially aligned with a central support member of the intrauterine device. The central support member (not shown) may be positioned along the axis 608 shown in FIGS. 10A to 10C. The central support member may be included in the applicator structure and coupled to the deployment mechanism 602. In the deployed position of the deployment mechanism 602, the ribbon bumper 600 may substantially flatten along a direction substantially perpendicular to the central support member positioned along axis 608 of the intrauterine device, as shown in FIG. 10C. The ribbon configuration may allow good contact between the mesh array and the fundus such that it may not impact the ablation profile of the intrauterine ablation device.

Figure 11A:
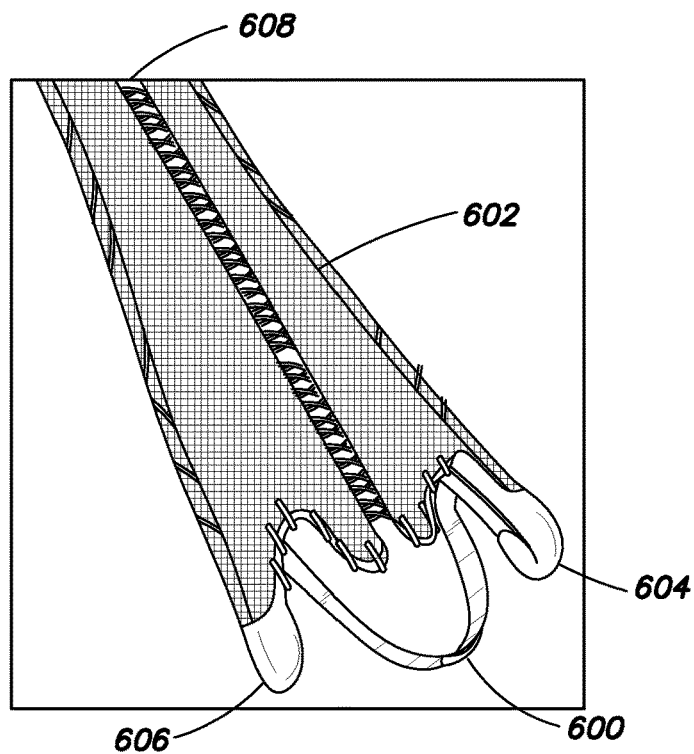
FIG. 11A is a perspective view of a portion of the intrauterine device of FIG. 10A in the partially deployed state according to aspects of the present invention.
Figure 11B:
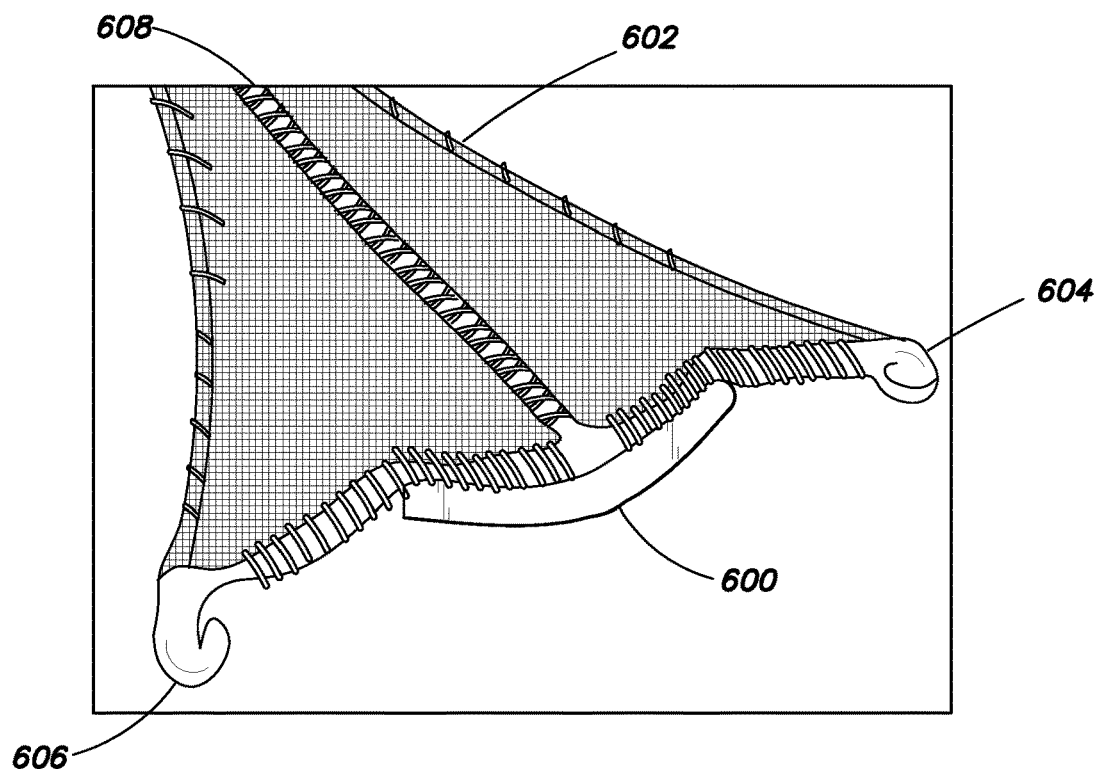
FIG. 11B is a perspective view of a portion of the intrauterine device of FIG. 11A in a deployed position according to aspects of the present invention.

FIG. 11A is a perspective view of a portion of the intrauterine device of FIG. 10A, illustrating the ribbon bumper 600, the deployment mechanism 602, the tips 604 and 606 and the axis 608 along which a central support member is aligned, as described previously in relation to FIGS. 10A to 10C. FIG. 11B is a perspective view of the embodiment of the intrauterine device of FIG. 11A in a deployed position.

Some embodiments including a bumper coupled to the deployment mechanism, such that the bumper automatically retracts as the deployment mechanism deploys, may function passively. In these embodiments, the bumper may not be controlled independently from the deployment mechanism. Therefore, there may be no need for an additional support member for the bumper. In other embodiments, such as that illustrated in FIGS. 3 to 6, the bumper may be coupled to an independently controlled central support member. The independently controlled central support member may include grips and springs in the proximal part of the intrauterine device.

FIGS. 12-17 illustrate some examples of applicator structures and deployment mechanisms that may be used, for example, in various embodiments of an intrauterine device having a bumper according to aspects of the present disclosure.

Figure 12:
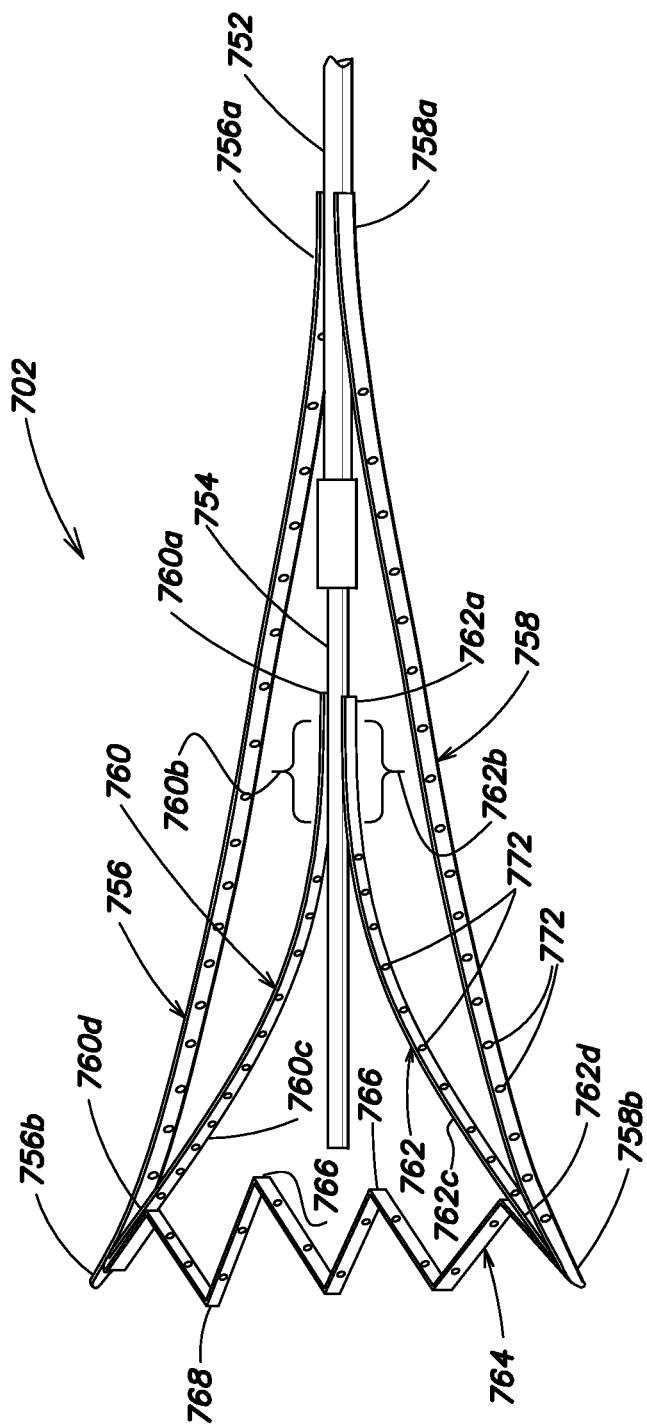
FIG. 12 is a perspective view of a portion of an exemplary embodiment of an intrauterine device in a deployed position according to aspects of the present invention.
Figure 13:
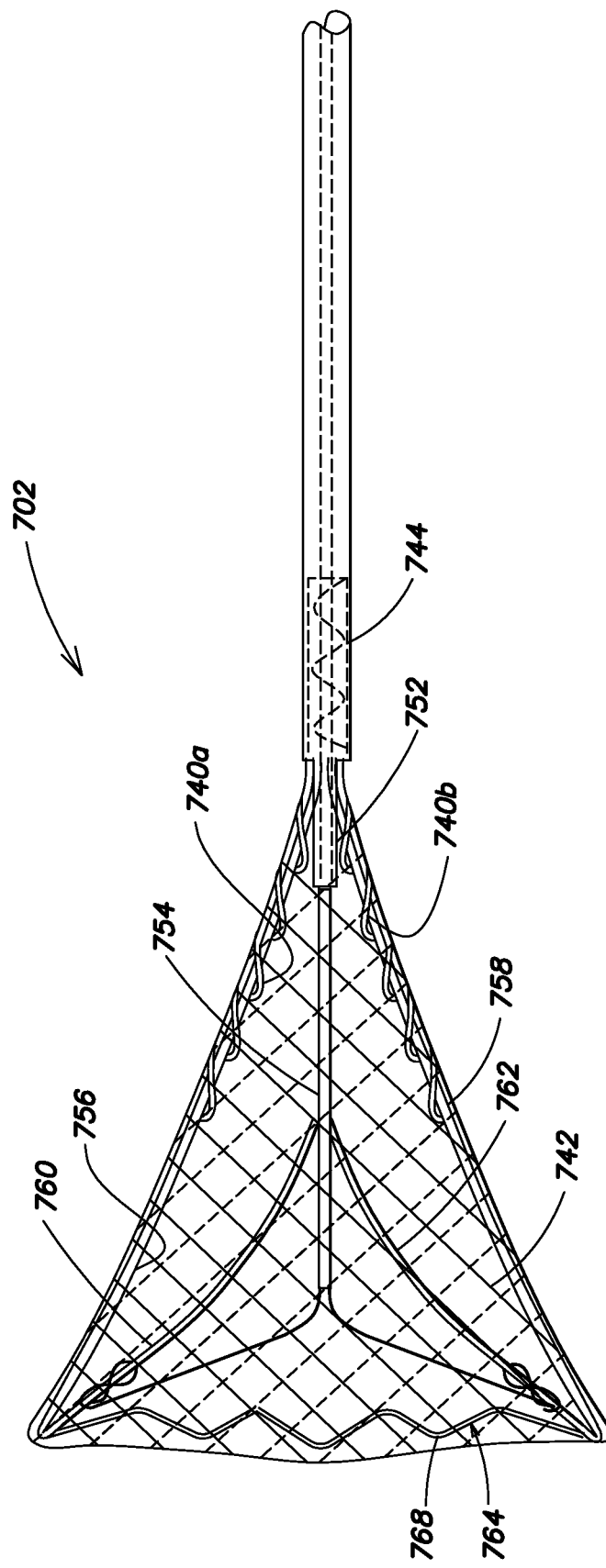
FIG. 13 is an elevation view of a portion of the intrauterine device of FIG. 12 further illustrating a mesh array according to aspects of the present invention.

FIGS. 12 and 13 illustrate an intrauterine device applicator structure 702 in a deployed position. The applicator structure 702 may include a mesh array 742 as shown in FIG. 13. In some embodiments, the deployment mechanism may be configured to spread the mesh array 742 from a collapsed state into a deployed state. In some embodiments, the mesh array is knit from elastic yarn, so a certain level of force is needed simply to spread the mesh array to the desired shape. In addition to stretching the mesh array, the deployment mechanism must be capable of generating additional spreading force to ensure that the deployment mechanism still opens properly if resistance is encountered. Simultaneously, it is desirable for the deployment mechanism to be as small as possible and to be as mechanically durable as possible.

In some embodiments, the deployment mechanism includes internal flexures (see 760, 762 of FIGS. 12 and 13) and external flexures (see 756, 758 of FIGS. 12 and 13). In a deployed position, external flexures (756, 758 of FIGS. 12 and 13) define the outer contour of the structure, and internal flexures (760, 762 of FIGS. 12 and 13) facilitate reliable deployment of the structure from the sheath into a collapsed position and into a deployed position as well as retraction of the structure into the collapsed position and into the sheath.

The structure 702 of FIGS. 12 and 13 may be spread open by driving an internal central support member 754 forward relative to an external central support member 752. Depending on the forces provided by the drive mechanism used to actuate the internal central support member, the applicator structure may or may not open to its maximum width. In some embodiments, the intrauterine device may include a compliant element, such as a spring, between the drive mechanism and the internal central support member 754. The spring transmits force to the internal central support member, so that if the external flexures are unrestricted, the flexures will deploy normally to their full width. Alternatively, in the event that the tips of the flexures somehow become restricted, the spring can absorb driving force, allowing the flexures to rest at a sub-maximum width without heavy stress. Thus, the introduction of a compliant element allows for a simple drive mechanism that drives a deployment mechanism that can automatically open to variable maximum widths (i.e. opening to fill a cavity of unknown size). It also controls the spreading force that the deployment mechanism is able to generate.

Referring to FIG. 12, the applicator structure 702 includes an external central support member 752, an internal central support member 754, external flexures 756 and 758 and internal flexures 760 and 762. The proximal end of the internal central support member 754 is coupled to the distal end of the external central support member 752, so as to provide a telescoping arrangement. The proximal ends 756a and 758a of the external flexures 756 and 758 are attached to the outside of the external central support member 752 near the distal end of the external support member 752. The proximal ends 760a and 762a of the internal flexures 760 and 762 are attached to the outside of the internal central support member 754, near the proximal end of the internal central support member 754. It is to be appreciated that in other embodiments, the proximal ends 760a and 762a of the internal flexures 760 and 762 may be attached to the inside of the internal central support member 754, or the proximal ends 760a and 762a of the internal flexures 760 and 762 may be attached into the wall of the internal central support member 754. The external flexures 756 and 758 and the internal flexures 760 and 762 are attached to the external 752 and internal 754 support members such that the external flexures 756 and 758 and internal flexures 760 and 762 lie in the same plane.

The external flexures 756 and 758 in one position extend outward away from being parallel with the central support members 752 and 754 to form a V-shape. According to one embodiment, the external flexures 756 and 758 extend laterally away from the external central support member 752, flaring outwards toward the distal ends 756*b* and 758*b*. Similarly, the internal flexures 760 and 762 extend laterally away from the internal central support member 754, forming a flared V-shape. The second sections 760*b* and 762*b* of the internal flexures 760 and 762, adjacent to the proximal ends 760*a* and 762*a*, gradually extend laterally away from the internal central support member 754. A third section 760*c* and 762*c* of each internal flexure 760 and 762 extends substantially laterally and longitudinally away from the internal central support member 754. The distal end 760*d* of the first internal flexure 760 is attached to a distal end 756*b* of the first external flexure 756, and a distal end 762*d* of the second internal flexure 762 is attached to the distal end 758*b* of the second external flexure 758.

As shown in FIG. 12, the central support member of the device applicator structure 702 includes external central support member 752 coupled to internal central support member 754. In other embodiments, the applicator structure 702 may include three or more support members coupled together. The external 752 and internal 754 central support members may move relative to one another. In one example, the external 752 and internal 754 central support members may be telescoping support members. In another example, the external 752 and internal 754 central support members may be slidably coupled together.

Figure 14:
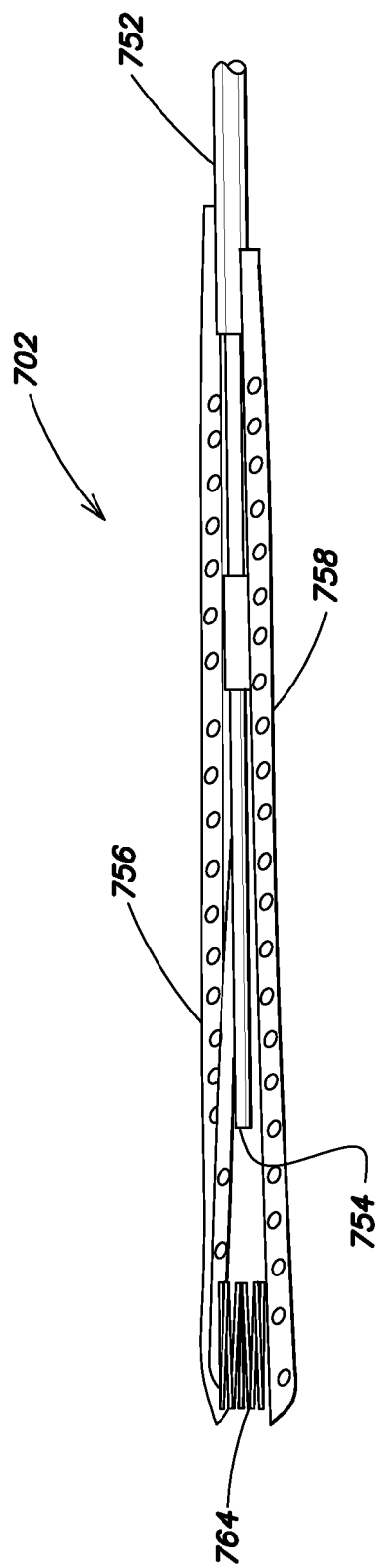
FIG. 14 is a perspective view of a portion of the intrauterine device of FIG. 12 in a collapsed position according to aspects of the present invention.

In some embodiments, as shown in FIG. 12, a transverse ribbon 764 may extend between the distal ends 756*b* and 758*b* of the external flexures 756 and 758. In one example, the transverse ribbon 764 may be configured to provide lateral support for a mesh array. In one embodiment, the transverse ribbon has a corrugated shape, and includes a plurality of creases 766 and 768, such that when the intrauterine device is in the collapsed position, as shown in FIG. 14, the transverse ribbon 764 is folded along the creases 766 and 768. In some embodiments, the transverse ribbon may be configured to be a ribbon bumper as described for example in relation with FIGS. 10A-10C and 11A-11B. In other embodiments, the intrauterine device may include a bumper in addition to the transverse ribbon. In one example, the bumper may be coupled to a second central support member as shown for example in FIG. 4 and the transverse ribbon may provide an opening to allow the second central support member to pass through it. The ribbon bumper may be configured to prevent a distal end of the applicator structure from becoming buried in the fundus tissue of the uterus of a patient, and the transverse ribbon may be configured to provide lateral support for the applicator structure. In yet other embodiments, as will be described for example in relation with FIGS. 15-17, the intrauterine device may not include a transverse ribbon.

Referring back to FIG. 12, according to one embodiment, the external central support member 752 and the internal central support member 754 are hollow elongate tubes. When a suction is applied to the applicator structure 702, for example from the suction source 112 shown in FIG. 1, fluid, vapor, liquid, and/or tissue may be suctioned through hollow elongate tubular internal support member 754, away from the patient.

According to one embodiment, the external flexures 756, 758 and internal flexures 760, 762 include multiple apertures 772. During use inside a patient, the apertures allow fluid, vapor, liquid and/or tissue to flow through the flexures and move within the uterus. In some embodiments, as shown in the illustrative embodiment, the transverse ribbon 764 also includes multiple apertures.

FIG. 13 is a perspective view of the applicator structure 702 in a deployed position and having a mesh array 742. The mesh array 742 surrounds the applicator structure 702. As previously discussed, the mesh array 742 may be knitted from a nylon and spandex knit and plated with gold, silver, or another conductive material. The mesh array 742 is conformable, permeable, and carries current. The mesh array 742 is attached to the external flexures 756, 758 with strands of thread 740*a* and 740*b*. The strands of thread 740*a*, 740*b* may be nylon. The strands of thread 740*a*, 740*b* are sewn through the mesh array 742 and around the external flexures 756, 758.

FIG. 14 is a perspective view of the applicator structure 702, illustrating the deployment mechanism in a collapsed position. In the collapsed position, the external flexures 756, 758 and the internal flexures 760, 762 of the deployment mechanism extend substantially parallel with the external 752 and internal 754 central support members of the applicator structure 702. The transverse ribbon 764 is folded along the creases 766, 768 shown in FIG. 12. The applicator 102 described with respect to FIG. 1 may include the applicator structure 702 of FIG. 4. During use of an intrauterine device, such as the device 100 described with respect to FIG. 1, the applicator structure 702 may be in a collapsed position inside the sheath 104 while the sheath 104 is inserted through the cervix. When the applicator 102 is extended distally from the distal end of the sheath 104, it expands to the deployed position shown in FIG. 12.

Figure 15:
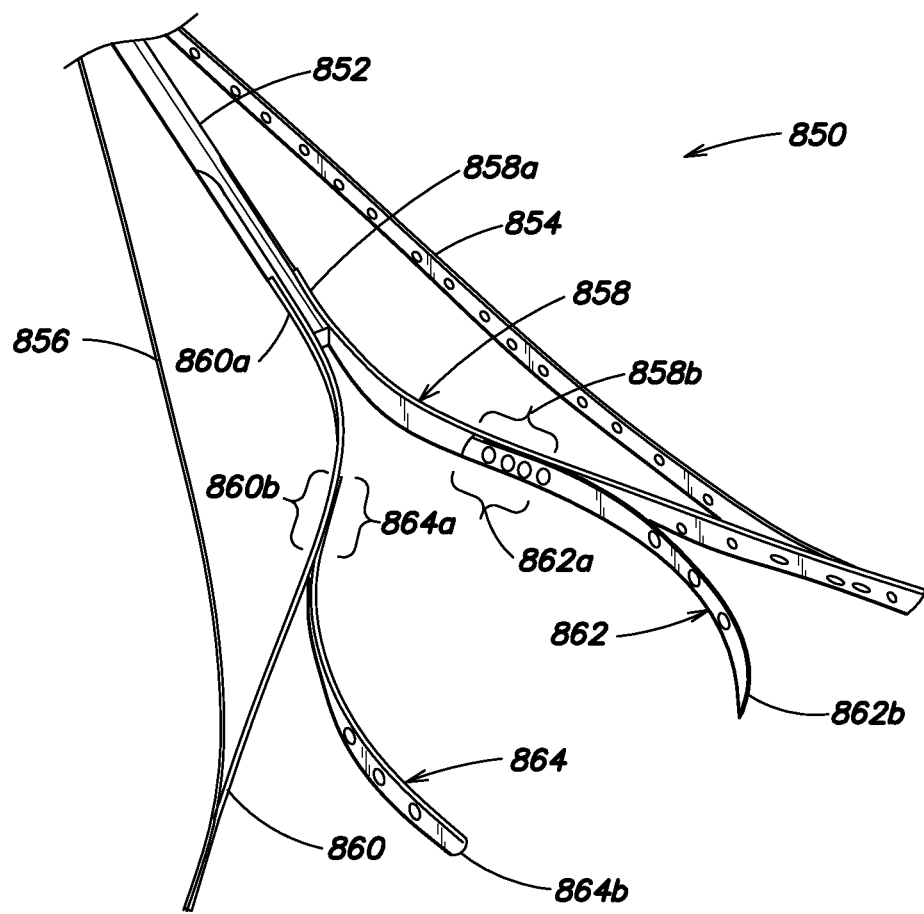
FIG. 15 is a perspective view of a portion of an exemplary embodiment of an intrauterine device in a deployed position according to aspects of the present invention.
Figure 16:
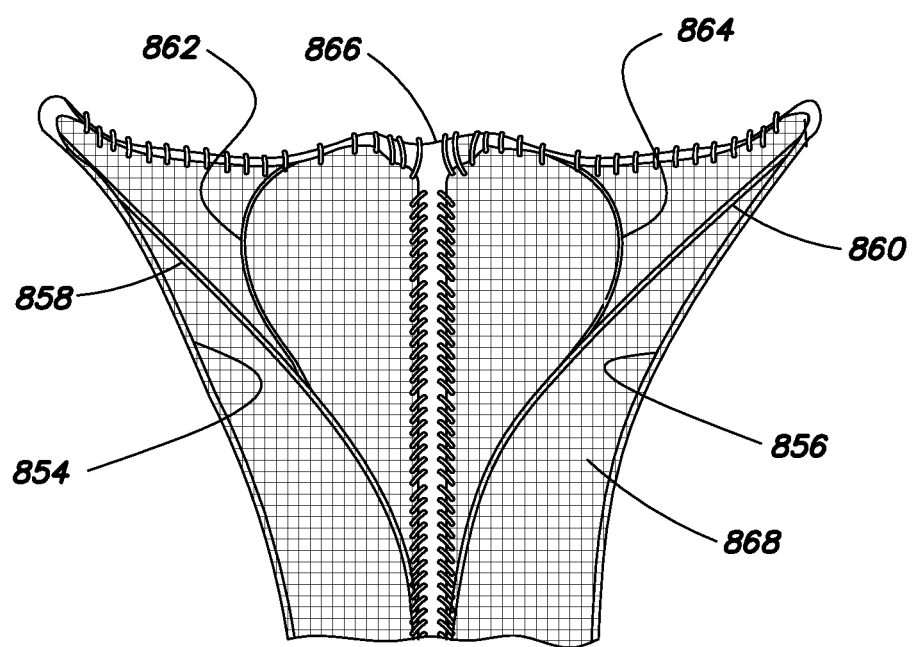
FIG. 16 is an elevation view of a portion of the intrauterine device of FIG. 15 further illustrating a mesh array according to aspects of the present invention.
Figure 17:
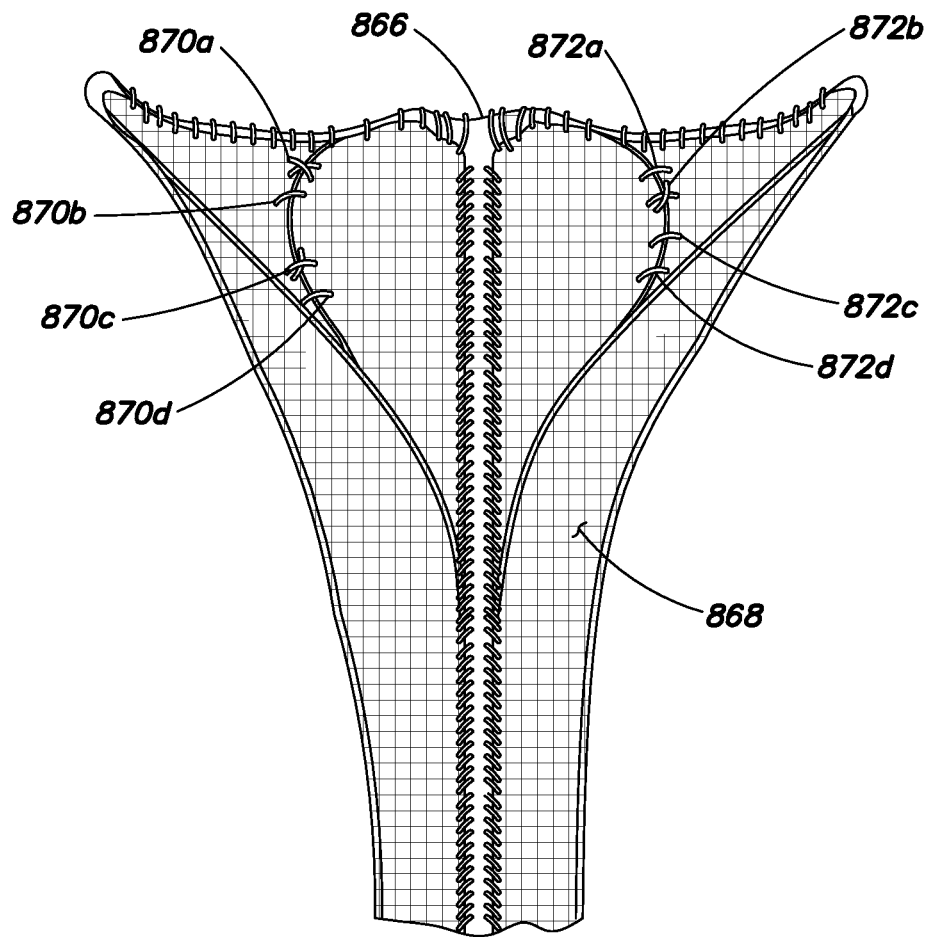
FIG. 17 is an elevation view of a portion of the intrauterine device of FIG. 16 according to aspects of the present invention.

According to any of the embodiments disclosed herein, the ribbon 764 shown by way of example in FIGS. 12 and 13 may be replaced with alternative mesh support designs. It is appreciated that the ribbon 764 shown in FIGS. 12 and 13 may take up a substantial amount of cross-sectional space in the collapsed position, as shown by way of example in FIG. 14. FIGS. 15-17 show portions of intrauterine devices with alternative embodiments of arms to support a mesh array. The arms may be used in place of a ribbon, for example, to reduce the outer diameter of an intrauterine device in a collapsed position. Reducing the outer diameter of an intrauterine device improves its ease of insertion and decreases patient discomfort. According to various examples, the mesh support arms mechanically support the distal end of the mesh array, preventing the mesh array from pulling back proximally and/or toward the central support members. Additionally, the mesh support arms provide vertical support, mechanically separating the top of the mesh array from the bottom of the mesh array, which may help prevent an alternating current short through the mesh array when energy is delivered to the medical device after it is inserted in a patient.

FIG. 15 is a perspective view of a portion of another embodiment of an intrauterine ablation device applicator structure 850 having arms 862, 864 shown in an expanded position. The applicator structure 850 includes a central support member 852, external flexures 854, 856, internal flexures 858, 860, and arms 862, 864. The proximal ends 862*a*, 864*a* of the arms 862, 864 are coupled to a middle portion 858*b*, 860*b* of the internal flexures 858, 860. The arms 862, 864 curve laterally outward, and then curve back in toward the center line defined by the central support member 852. The distal ends 862*b*, 864*b* of the arms 862, 864 are directed inward toward the center line.

FIG. 16 is an elevation view of a portion of the intrauterine ablation device applicator structure 850 of FIG. 15 with a mesh array cover 868 disposed thereabout. FIG. 17 is an elevation view of a portion of the intrauterine ablation device applicator structure 850 of FIG. 15 having a mesh array anchored to the arms 862, 864 in multiple locations 870a-d, 872a-d. By anchoring the arms to the array in one or more locations, the system relies on the combined strength of the arms interacting with the array, providing improved mechanical strength and robustness of the system without increasing the size of the arms. According to one feature, the arms 862, 864 prevent the top and bottom parts of the mesh array from coming in contact with one another. According to another feature, the arms 862, 864 prop up the distal end of the mesh array.

As discussed above, decreasing the thickness of the structure that maintains the extension of the mesh array at the distal end of the applicator structure 852 allows for a decreased outer diameter of a sheath enclosing the applicator structure 852 in a retracted position. The applicator structure 852 includes only two arms 862, 864, which are attached to the internal flexures 858, 860 distal to the distal end of the central support member 852. Thus, the applicator structure 852 can be positioned within a substantially smaller diameter sheath in the retracted position than, for example, the applicator structure 702 shown in FIGS. 12-14.

The applicator structure 850 described with respect to FIGS. 15-17 may be included in the various embodiments of the intrauterine devices as described for example in FIGS. 3-6 and FIGS. 10A-10C. In one embodiment, the applicator 210 of FIG. 4 may be the applicator structure 850 of FIG. 15, the mesh array 214 may be the mesh array 868 illustrated in FIGS. 16 and 17 and the deployment mechanism 212 may include for example the flexures 854, 856, 858, 860 of the applicator structure 850 of FIG. 15. In one embodiment, a bumper may be coupled to an independently controlled central support member that extends through the central stripe 866 of the mesh array 868 as shown in FIGS. 16 and 17. In another embodiment, a ribbon bumper as described for example with respect to FIGS. 10A to 10C may be included in an intrauterine device having the applicator structure 850 of FIGS. 15-17.

Figure 18:
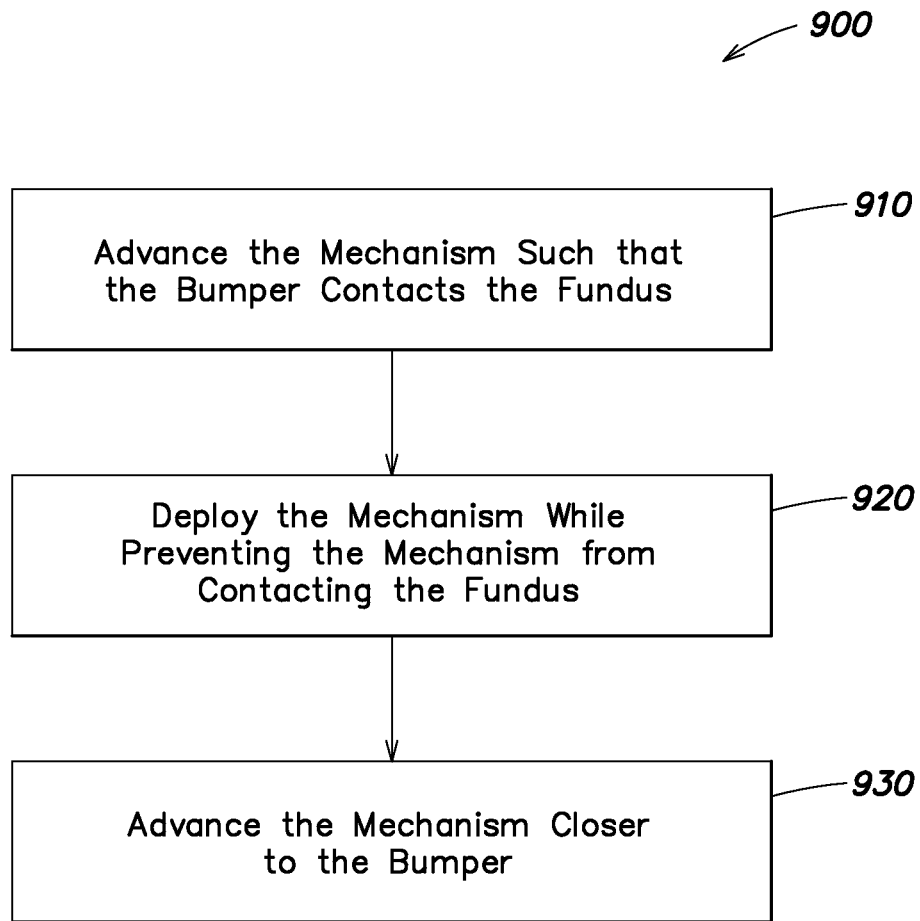
FIG. 18 illustrates one embodiment of a method for facilitating the deployment of a mechanism of an intrauterine device according to aspects of the present invention.

According to another aspect of the present disclosure, methods of facilitating deployment of an intrauterine device may be provided. FIG. 18 illustrates one example of a method 900 for easier deployment of an intrauterine device having a deployment mechanism, using a bumper. The method 900 may include providing or obtaining an intrauterine device having a bumper according to aspects disclosed herein. The bumper may be positioned at a more distal position relative to a distal end of a structure including the deployment mechanism of the intrauterine device. The bumper may be at a more distal position with the deployment mechanism in a collapsed state. For example, the bumper may be positioned as shown in the various embodiments illustrated in FIG. 3, FIG. 7A, FIG. 8A, FIG. 9A and FIG. 10A.

Method 900 may include an act 910 of advancing the structure with the deployment mechanism in a collapsed state through the cervical canal and into the uterus of a patient such that the bumper contacts the fundus tissue, as illustrated for example in FIG. 8A.

The method 900 may include an act 920 of deploying the deployment mechanism such that the bumper prevents the deployment mechanism, and more generally a distal end of the structure during deployment of the deployment mechanism, as shown for example in FIG. 8B. Deploying the deployment mechanism may include maintaining the bumper in contact with the fundus during deployment. Deploying the deployment mechanism may include extending the deployment mechanism from a collapsed state or position substantially aligned with a central support member of the intrauterine device (as shown for example in FIG. 3) to a deployed state or position flexing away from the central support member (as shown for example in FIG. 4). The method 900 may further include an act of retracting the bumper. For example, the bumper may be retracted to be substantially aligned with a distal end of the structure (such as the tips of the structure as shown for example in FIG. 7B). In another example, the bumper may be retracted to be more proximal than a distal end of the structure.

The method 900 may further include an act 930 of advancing the structure including the deployment mechanism relative to the bumper, as shown for example in FIG. 8C. Therefore, in the deployed position, the deployment mechanism or the structure that includes the deployment mechanism may be positioned at the distal end of the intrauterine device. Advancing the deployment mechanism or the applicator structure may include or may be performed simultaneously with an act of retracting the bumper relative to the deployment mechanism or the applicator structure. Advancing the deployment mechanism relative to the bumper may further include positioning the deployment mechanism such that the deployment mechanism or the structure that includes the deployment mechanism contacts the fundus.

In some embodiments, advancing the deployment mechanism into the uterus, such as in act 910, may at least partially overlap with deploying the deployment mechanism from a collapsed to a deployed position, such as in act 920. In some embodiments, deploying or extending the deployment mechanism from a collapsed to a deployed position, such as in act 920, may at least partially overlap with advancing the deployment mechanism relative to the bumper, such as in act 930. Advancing the deployment mechanism relative to the bumper may include positioning the deployment mechanism such that the deployment mechanism contacts the fundus. In some embodiments, extending the deployment mechanism may further include extending the deployment mechanism such that the deployment mechanism contacts the fundus in the deployed position. In some embodiments, acts of retracting the bumper and deploying the deployment mechanism from a collapsed to a deployed position may overlap at least partially. In some embodiments, retracting the bumper may include flattening the bumper. The bumper may be gradually flattened while the deployment mechanism is gradually deployed, as shown for example in FIG. 9B and FIGS. 10A to 10C. The bumper may be flattened such that the bumper is aligned substantially with a distal end of the structure. In some embodiments, the act of retracting the bumper may include telescoping a second support member attached to the bumper with a first central support member coupled to the deployment mechanism.

Although various embodiments have been described as facilitating deployment of intrauterine devices, it is to be appreciated that embodiments of the intrauterine devices and methods disclosed herein may also be used to facilitate contracting or collapsing the deployment mechanism from a deployed position to a collapsed position. For example, the bumper may prevent a distal end of the applicator structure from becoming buried in the fundus tissue during contraction of the deployment mechanism. In some embodiments, the bumper may be retracted in the deployed position to allow a mesh array to contact the fundus during application. Following therapy application, the bumper may be advanced so as to prevent the mesh array or a distal end of the applicator structure from contacting the fundus prior to contracting the applicator structure. In some embodiments having a ribbon bumper coupled to the deployment mechanism, such as shown in FIGS. 10A to 10C, as the deployment mechanism contracts from a deployed position to a collapsed position, the ribbon bumper gradually advances so as to prevent the distal end of the applicator structure or the deployment mechanism from contacting the fundus.

In one embodiment, the method 900 of FIG. 18 may further include acts to facilitate collapsing the deployment mechanism of an intrauterine device. For example, the method may further include one or more of retracting the deployment mechanism away from the bumper such that the deployment mechanism does not contact the fundus, collapsing the deployment mechanism from a deployed position to a collapsed position while preventing the deployment mechanism from contacting the fundus, and retracting the collapsed deployment mechanism and the bumper away from the fundus. The collapsed deployment mechanism may be retracted into a sheath for removal from the patient. In some embodiments, the bumper may also be retracted into the sheath.

Another aspect is directed to providing an intrauterine device having a flange configured to facilitate deployment of a mechanism of the intrauterine device while preventing a distal end of the mechanism from being buried in the fundus tissue during deployment, as shown in FIGS. 19A and 19B.

FIG. 19A illustrates an exemplary embodiment of a portion of an intrauterine device having a flange and seated in the uterus in a collapsed position. The intrauterine device includes an applicator structure 1000 extending through a sheath 1002 into the uterus 1006. The intrauterine device further includes a flange 1004. The intrauterine device is configured such that a length of the device from the flange 1004 to the distal end of the applicator structure 1000 is less than the sounding length from the external os 1010 to the fundus 1008. As the flange 1004 abuts the external os 1010, the distal end of the applicator structure 1000 is offset from the fundus 1008. In one example, the offset may be around half a centimeter.

FIG. 19B illustrates the portion of the intrauterine device of FIG. 19A in a deployed position. As the applicator structure 1000 is deployed, the tips located at the distal end of the applicator structure move along the dotted lines and do not contact the fundus 1008. The applicator structure 1000 may be deployed while being advanced such that in the fully expanded position the offset between the distal end of the applicator structure and the fundus 1008 is eliminated. The applicator structure may include a deployment mechanism and a mesh array as described earlier and the tips may be array tips.

Figure 20:
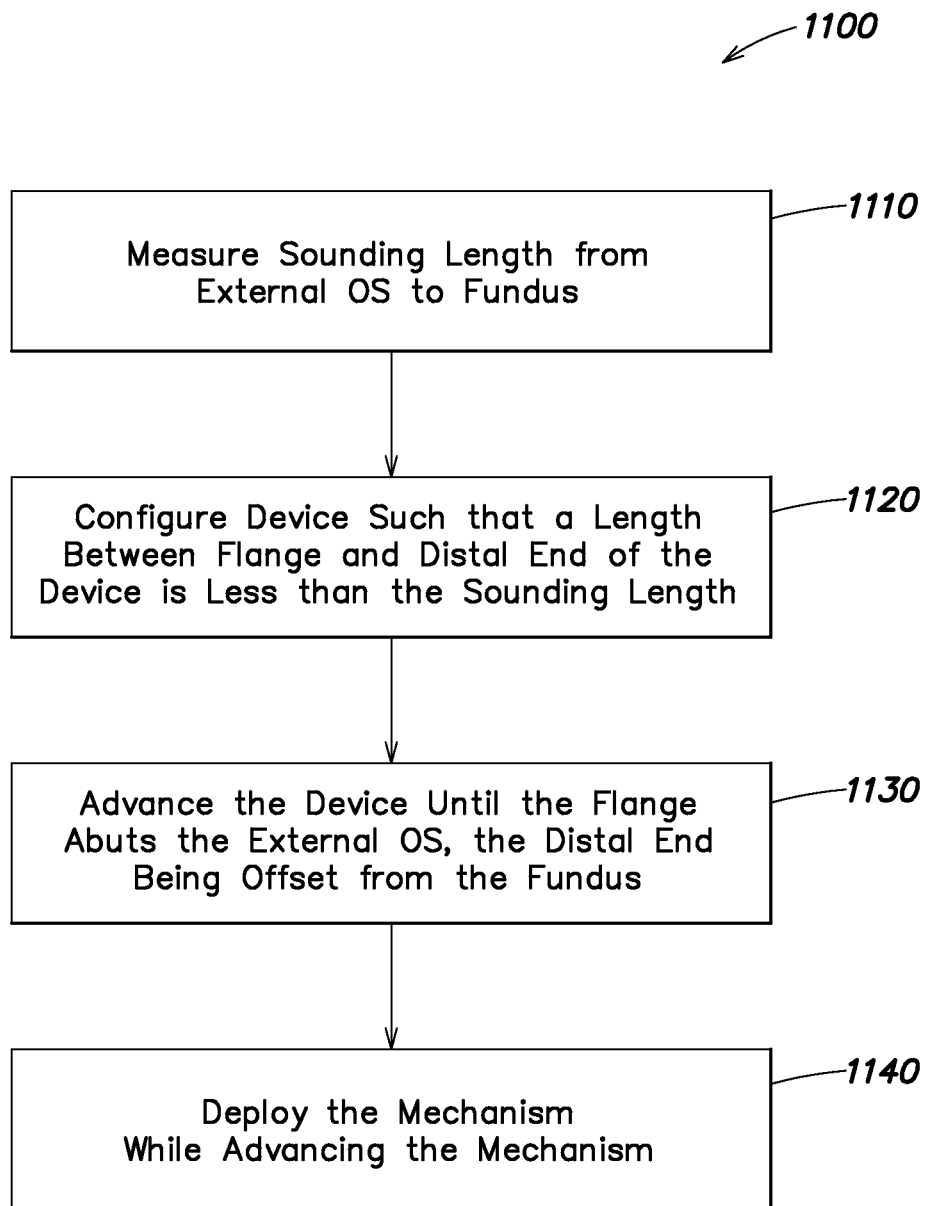
FIG. 20 illustrates one embodiment of a method for facilitating the deployment of a mechanism of an intrauterine device having a flange according to aspects of the present invention.

FIG. 20 illustrates one embodiment of a method for facilitating the deployment of a mechanism of an intrauterine device having a flange. For example, the intrauterine device may be the embodiment described with reference to FIGS. 19A and 19B. The method 1100 includes an act 1110 of measuring the sounding length from the external os to the fundus. The method further includes an act 1120 of configuring the intrauterine device such that the length between the flange and the distal end of the device is less than the sounding length, as shown for example in FIG. 19A. The method further includes an act 1130 of advancing the device into the uterus until the flange abuts the external os, resulting in an offset between the distal end of the device and the fundus, as shown in FIG. 19A. The method further includes an act 1140 of deploying the deployment mechanism while advancing the deployment mechanism as shown for example in FIG. 19B. In other embodiments, the deployment mechanism may be advanced to eliminate the offset after deploying the mechanism.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only, and the scope of the disclosure should be determined from proper construction of the appended claims, and their equivalents.

What is claimed is:

1. An intrauterine ablation device, comprising:
a central support member;
a first flexure coupled to a distal end portion of the central support member, the first flexure having a first flexure distal free end;
a second flexure coupled to the distal end portion of the central support member, the second flexure having a second flexure distal free end, wherein the first and second flexures are adjustable between a collapsed configuration, in which the first and second flexure distal free ends are closely apposed to one another for transcervical introduction into a uterus, and an expanded configuration, in which the first and second flexure distal free ends extend laterally away from one another in opposite directions; and
a distal bumper coupled to a distal end of the central support member, wherein the distal bumper is positioned distally of the first and second flexure distal free ends when the first and second flexures are is in the collapsed configuration, and wherein the distal bumper prevents the first and second flexure distal free ends from engaging a fundal wall of the uterus during a transition of the first and second flexures from the collapsed configuration to the expanded configuration.

2. The intrauterine ablation device of claim 1, wherein the distal bumper is configured to conform to the fundal wall when the first and second flexures are in the expanded configuration.

3. The intrauterine ablation device of claim 2, wherein the distal bumper comprises a flexible ribbon and/or a thin flexible membrane.

4. The intrauterine ablation device of claim 1, wherein the distal bumper extends transversely between the first and second flexures when the first and second flexures are in the expanded configuration.

5. The intrauterine ablation device of claim 1, wherein an outer surface of the distal bumper extends from a first end to a second end of the distal bumper, and wherein the first end of the distal bumper contacts the first flexure, and wherein the second end of the distal bumper contacts the second flexure.

6. The intrauterine ablation device of claim 1, wherein the distal bumper comprises an electrically conductive material.

7. The intrauterine ablation device of claim 6, wherein the distal bumper comprises a porous material, a hydrophilic material, a conductive polymer, a material infused with an electrically conductive particulate, or a combination of said materials.

8. The intrauterine ablation device of claim 1, further comprising a tubular member, wherein the central support member is at least partially slidably disposed within the tubular member.

9. The intrauterine ablation device of claim 1, wherein the distal bumper has a curved shape when the first and second flexures are in the expanded configuration.

10. The intrauterine ablation device of claim 1, wherein the distal bumper is configured to maintain separation between the fundal wall and the first and second flexure distal free ends as the first and second flexures transitions from the collapsed configuration to the expanded configuration.

11. The intrauterine ablation device of claim 1, further comprising a flexible tissue contacting member overlaying the first and second flexures and configured for delivering ablative energy to an endometrial lining of the uterus,
   wherein the distal bumper is coupled to the tissue contacting member.

12. An intrauterine ablation device, comprising:
   a central support member; and
   an energy applicator operatively coupled to a distal end portion of the central support member, the energy applicator comprising
   a first flexure coupled to a distal end portion of the central support member, the first flexure having a first flexure distal free end,
   a second flexure coupled to the distal end portion of the central support member, the second flexure having a second flexure distal free end, wherein the first and second flexures are adjustable between a collapsed configuration, in which the first and second flexure distal free ends are closely apposed to one another so that the energy applicator is configured for transcervical introduction into a uterus, and an expanded configuration, in which the first and second flexure distal free ends extend laterally away from one another in opposite directions,
   a flexible tissue contacting member overlaying the first and second flexures and configured for delivering ablative energy to an endometrial lining of the uterus, and
   a distal bumper coupled to the tissue contacting member and configured to prevent the first and second flexure distal free ends from engaging a fundal wall of the uterus during a transition of the first and second flexures from the collapsed configuration to the expanded configuration.

13. The intrauterine ablation device of claim 12, wherein an outer surface of the distal bumper extends from a first end to a second end of the distal bumper, and wherein the first end of the distal bumper contacts the first inner flexure, and wherein the second end of the distal bumper contacts the second inner flexure.

14. The intrauterine ablation device of claim 12, wherein the distal bumper has a curved shape when the first and second flexures are in the expanded configuration.

* * * * *